United States Patent
Willis et al.

(10) Patent No.: US 12,350,497 B2
(45) Date of Patent: Jul. 8, 2025

(54) TISSUE STIMULATION SYSTEMS AND METHODS, SUCH AS FOR PACING CARDIAC TISSUE

(71) Applicant: EBR Systems, Inc., Sunnyvale, CA (US)

(72) Inventors: Nathaniel Parker Willis, Sunnyvale, CA (US); Richard Riley, Sunnyvale, CA (US); Timothy A. Fayram, Sunnyvale, CA (US)

(73) Assignee: EBR SYSTEMS, INC., Sunnyvale, CA (US)

(*) Notice: Subject to any disclaimer, the term of this patent is extended or adjusted under 35 U.S.C. 154(b) by 548 days.

(21) Appl. No.: 17/668,771

(22) Filed: Feb. 10, 2022

(65) Prior Publication Data

US 2023/0248980 A1   Aug. 10, 2023

(51) Int. Cl.
*A61N 1/365* (2006.01)
*A61N 1/05* (2006.01)
(Continued)

(52) U.S. Cl.
CPC ....... *A61N 1/36514* (2013.01); *A61N 1/0563* (2013.01); *A61N 1/37211* (2013.01);
(Continued)

(58) Field of Classification Search
CPC .............. A61N 1/36514; A61N 1/0563; A61N 1/37223; A61N 1/3787; A61N 1/3621;
(Continued)

(56) References Cited

U.S. PATENT DOCUMENTS 3,057,356 A   10/1962 Wilson
3,659,615 A   5/1972 Enger
(Continued)

FOREIGN PATENT DOCUMENTS

DE   4330680 A1   3/1995
EP   2265166 A1   12/2010
(Continued)

OTHER PUBLICATIONS

U.S. Appl. No. 11/315,023, filed Dec. 21, 2005, Cowan.
(Continued)

*Primary Examiner* — Brian T Gedeon
(74) *Attorney, Agent, or Firm* — Perkins Cole LLP

(57) ABSTRACT

The present technology is generally directed to implantable medical device systems for stimulating tissue, such as heart tissue. In some embodiments, an implantable medical device system includes a controller-transmitter and a receiver-stimulator in operable communication with one another. The receiver-stimulator can be implanted at the heart of a patient. The controller-transmitter can be configured to transmit an acoustic signal to the receiver-stimulator, which receives the acoustic signal and converts the acoustic signal to electrical energy for delivery to the heart via one or more stimulation electrodes. The receiver-stimulator can further be configured to transmit a radiofrequency signal to the controller-transmitter including information about sensed physiological parameters of the patient, status information, and the like.

11 Claims, 7 Drawing Sheets

(51) Int. Cl.
  *A61N 1/362* (2006.01)
  *A61N 1/372* (2006.01)
  *A61N 1/378* (2006.01)

(52) U.S. Cl.
  CPC ..... *A61N 1/37217* (2013.01); *A61N 1/37252* (2013.01); *A61N 1/3787* (2013.01); *A61N 1/3621* (2013.01)

(58) Field of Classification Search
  CPC ............ A61N 1/37252; A61N 1/37211; A61N 1/37217; A61N 1/37276; A61N 1/37282; A61N 1/37288
  See application file for complete search history.

(56) References Cited

U.S. PATENT DOCUMENTS

| | | |
|---|---|---|
| 3,693,627 A | 9/1972 | Berkovits |
| 3,698,398 A | 10/1972 | Berkovits |
| 3,735,756 A | 5/1973 | Richards et al. |
| 3,832,994 A | 9/1974 | Bicher et al. |
| 3,835,865 A | 9/1974 | Bowers |
| 3,857,382 A | 12/1974 | Williams et al. |
| 3,893,461 A | 7/1975 | Preston |
| 3,939,844 A | 2/1976 | Peuignot et al. |
| 3,942,534 A | 3/1976 | Allen et al. |
| 4,181,133 A | 1/1980 | Kolenik et al. |
| 4,256,115 A | 3/1981 | Bilitch |
| 4,265,228 A | 5/1981 | Zoll |
| 4,280,502 A | 7/1981 | Baker et al. |
| 4,343,312 A | 8/1982 | Cals et al. |
| 4,373,531 A | 2/1983 | Wittkampf |
| 4,399,818 A | 8/1983 | Money |
| 4,498,478 A | 2/1985 | Bourgeois |
| 4,561,442 A | 12/1985 | Vollmann et al. |
| 4,577,633 A | 3/1986 | Berkovits |
| 4,651,716 A | 3/1987 | Forester et al. |
| 4,651,740 A | 3/1987 | Schroeppel |
| 4,690,144 A | 9/1987 | Rise et al. |
| 4,830,006 A | 5/1989 | Haluska et al. |
| 5,018,523 A | 5/1991 | Bach, Jr. et al. |
| 5,063,928 A | 11/1991 | Grevis et al. |
| 5,103,129 A | 4/1992 | Slayton et al. |
| 5,113,859 A | 5/1992 | Funke |
| 5,141,588 A | 8/1992 | VanBuskirk |
| 5,165,403 A | 11/1992 | Mehra |
| 5,170,784 A | 12/1992 | Ramon et al. |
| 5,174,289 A | 12/1992 | Cohen |
| 5,186,177 A | 2/1993 | O'Donnell et al. |
| 5,193,539 A | 3/1993 | Schulman et al. |
| 5,292,338 A | 3/1994 | Bardy et al. |
| 5,377,166 A | 12/1994 | Kuhn |
| 5,405,367 A | 4/1995 | Schulman et al. |
| 5,411,535 A | 5/1995 | Fujii et al. |
| 5,433,731 A | 7/1995 | Hoegnelid et al. |
| 5,557,210 A | 9/1996 | Cappa |
| 5,590,657 A | 1/1997 | Cain et al. |
| 5,674,251 A | 10/1997 | Combs et al. |
| 5,749,909 A | 5/1998 | Schroeppel et al. |
| 5,751,539 A | 5/1998 | Stevenson et al. |
| 5,757,104 A | 5/1998 | Getman et al. |
| 5,766,227 A | 6/1998 | Nappholz et al. |
| 5,782,880 A | 7/1998 | Lahtinen |
| 5,800,464 A | 9/1998 | Kieval |
| 5,814,089 A | 9/1998 | Stokes et al. |
| 5,817,130 A | 10/1998 | Cox et al. |
| 5,843,136 A | 12/1998 | Zhu |
| 5,844,349 A | 12/1998 | Oakley et al. |
| 5,871,506 A | 2/1999 | Mower |
| 5,879,303 A | 3/1999 | Averkiou et al. |
| 5,935,158 A | 8/1999 | Holmstrom et al. |
| 5,978,204 A | 11/1999 | Stevenson et al. |
| 5,998,910 A | 12/1999 | Park et al. |
| 6,037,704 A | 3/2000 | Welle |
| 6,070,101 A | 5/2000 | Struble et al. |
| 6,078,837 A | 6/2000 | Peterson et al. |
| 6,110,098 A | 8/2000 | Renirie et al. |
| 6,141,588 A | 8/2000 | Renirie et al. |
| 6,208,894 B1 | 3/2001 | Schulman |
| 6,223,079 B1 | 4/2001 | Bakels et al. |
| 6,233,484 B1 | 5/2001 | Ben-Haim et al. |
| 6,236,887 B1 | 5/2001 | Ben-Haim |
| 6,264,611 B1 | 7/2001 | Ishikawa et al. |
| 6,285,906 B1 | 9/2001 | Ben-Haim |
| 6,298,268 B1 | 10/2001 | Ben-Haim |
| 6,317,631 B1 | 11/2001 | Ben-Haim |
| 6,330,475 B1 | 12/2001 | Renirie et al. |
| 6,330,476 B1 | 12/2001 | Ben-Haim |
| 6,363,279 B1 | 3/2002 | Ben-Haim |
| 6,366,816 B1 | 4/2002 | Marchesi |
| 6,408,205 B1 | 6/2002 | Renirie et al. |
| 6,424,234 B1 | 7/2002 | Stevenson et al. |
| 6,425,869 B1 | 7/2002 | Rafter et al. |
| 6,428,484 B1 | 8/2002 | Battmer |
| 6,439,236 B1 | 8/2002 | Porter et al. |
| 6,442,424 B1 | 8/2002 | Ben-Haim |
| 6,445,953 B1 | 9/2002 | Bulkes et al. |
| 6,463,324 B1 | 10/2002 | Ben-Haim |
| 6,464,680 B1 | 10/2002 | Brisken et al. |
| 6,496,715 B1 | 12/2002 | Lee et al. |
| 6,522,926 B1 | 2/2003 | Kieval |
| 6,527,729 B1 | 3/2003 | Turcott |
| 6,534,895 B2 | 3/2003 | Kadota et al. |
| RE38,119 E | 5/2003 | Mower |
| 6,584,358 B2 | 6/2003 | Carter |
| 6,600,955 B1 | 7/2003 | Zierhofer |
| 6,628,989 B1 | 9/2003 | Penner et al. |
| 6,645,145 B1 | 11/2003 | Dreschel et al. |
| 6,647,292 B1 | 11/2003 | Bardy et al. |
| 6,654,638 B1 | 11/2003 | Sweeney |
| 6,671,547 B2 | 12/2003 | Lyster et al. |
| 6,834,204 B2 | 1/2004 | Osteroff et al. |
| 6,687,538 B1 | 2/2004 | Hrdlicka |
| 6,707,230 B2 | 3/2004 | Smith et al. |
| 6,721,597 B1 | 4/2004 | Bardy et al. |
| 6,725,093 B1 | 4/2004 | Ben-Haim |
| 6,728,576 B2 | 4/2004 | Thompson et al. |
| 6,754,528 B2 | 6/2004 | Bardy et al. |
| 6,754,531 B1 | 6/2004 | Kroll et al. |
| 6,764,446 B2 | 7/2004 | Wolinsky et al. |
| 6,788,974 B2 | 9/2004 | Bardy et al. |
| 6,795,732 B2 | 9/2004 | Stadler et al. |
| 6,798,716 B1 | 9/2004 | Charych |
| 6,856,835 B2 | 2/2005 | Bardy et al. |
| 6,970,742 B2 | 11/2005 | Mann et al. |
| 6,983,185 B2 | 1/2006 | Ley |
| 7,006,864 B2 | 2/2006 | Echt et al. |
| 7,010,350 B2 | 3/2006 | Kralik |
| 7,024,248 B2 | 4/2006 | Penner |
| 7,043,292 B2 | 5/2006 | Tarjan et al. |
| 7,050,849 B2 | 5/2006 | Echt et al. |
| 7,160,258 B2 | 1/2007 | Imran et al. |
| 7,184,830 B2 | 2/2007 | Echt et al. |
| 7,198,603 B2 | 4/2007 | Penner |
| 7,200,437 B1 | 4/2007 | Nabutovsky |
| 7,283,874 B2 | 10/2007 | Penner et al. |
| 7,349,740 B2 | 3/2008 | Soykan et al. |
| 7,489,967 B2 | 2/2009 | Von Arx et al. |
| 7,532,933 B2 | 5/2009 | Hastings |
| 7,558,631 B2 | 7/2009 | Cowan et al. |
| 7,606,621 B2 | 10/2009 | Brisken et al. |
| 7,610,092 B2 | 10/2009 | Cowan et al. |
| 7,702,392 B2 | 4/2010 | Echt |
| 7,751,881 B2 | 7/2010 | Cowan et al. |
| 7,765,001 B2 | 7/2010 | Echt |
| 7,848,815 B2 | 12/2010 | Brisken et al. |
| 7,890,173 B2 | 2/2011 | Brisken et al. |
| 7,894,907 B2 | 2/2011 | Cowan et al. |
| 7,899,541 B2 * | 3/2011 | Cowan ............... A61N 1/36007 607/40 |
| 7,996,087 B2 | 8/2011 | Cowan et al. |
| 8,007,227 B2 | 8/2011 | Rogall |
| 8,315,701 B2 | 11/2012 | Cowan et al. |
| 8,718,773 B2 | 5/2014 | Willis et al. |

(56) References Cited

U.S. PATENT DOCUMENTS

| | | | |
|---|---|---|---|
| 9,008,776 B2 | 4/2015 | Cowan et al. | |
| 9,283,392 B2 | 3/2016 | Moore | |
| 9,907,968 B2 | 3/2018 | Moore | |
| 10,080,903 B2 | 9/2018 | Willis | |
| 10,456,588 B2 | 10/2019 | Willis | |
| 2002/0077673 A1 | 6/2002 | Penner et al. | |
| 2003/0013974 A1 | 1/2003 | Natarjan et al. | |
| 2003/0069625 A1 | 4/2003 | Ley et al. | |
| 2004/0015104 A1 | 1/2004 | Goldberger | |
| 2004/0064166 A1 | 4/2004 | Thompson | |
| 2004/0106959 A1 | 6/2004 | Schmidt | |
| 2004/0162501 A1 | 8/2004 | Imran et al. | |
| 2004/0167580 A1 | 8/2004 | Mann et al. | |
| 2004/0172083 A1 | 9/2004 | Penner et al. | |
| 2004/0204744 A1 | 10/2004 | Penner et al. | |
| 2004/0243192 A1 | 12/2004 | Hepp et al. | |
| 2004/0260214 A1 | 12/2004 | Echt | |
| 2004/0260346 A1 | 12/2004 | Overall et al. | |
| 2005/0065426 A1 | 3/2005 | Porat | |
| 2005/0070962 A1 | 3/2005 | Echt et al. | |
| 2006/0009831 A1 | 1/2006 | Lau et al. | |
| 2006/0085039 A1 | 4/2006 | Hastings | |
| 2006/0106442 A1 | 5/2006 | Richardson et al. | |
| 2006/0135999 A1 | 6/2006 | Bodner et al. | |
| 2006/0136004 A1 | 6/2006 | Cowan | |
| 2006/0136005 A1 | 6/2006 | Brisken | |
| 2006/0161061 A1 | 7/2006 | Echt et al. | |
| 2006/0224067 A1 | 10/2006 | Giftakis et al. | |
| 2006/0241701 A1 | 10/2006 | Markowitz et al. | |
| 2007/0027508 A1 | 2/2007 | Cowan | |
| 2007/0032749 A1 | 2/2007 | Overall et al. | |
| 2007/0055184 A1 | 3/2007 | Echt | |
| 2007/0060961 A1 | 3/2007 | Echt | |
| 2007/0067000 A1 | 3/2007 | Strother | |
| 2007/0078490 A1 | 4/2007 | Cowan | |
| 2007/0088394 A1 | 4/2007 | Jacobson | |
| 2007/0088397 A1 | 4/2007 | Jacobson | |
| 2007/0088398 A1 | 4/2007 | Jacobson | |
| 2007/0150009 A1 | 6/2007 | Kveen et al. | |
| 2007/0232936 A1 | 10/2007 | Mann et al. | |
| 2007/0260286 A1 | 11/2007 | Giftakis et al. | |
| 2007/0265677 A1 | 11/2007 | Giftakis et al. | |
| 2007/0293912 A1 | 12/2007 | Cowan | |
| 2012/0203306 A1 | 8/2012 | Sarvazyan | |
| 2017/0225004 A1* | 8/2017 | Casse | A61N 2/02 |
| 2019/0313908 A1 | 10/2019 | Tommaso | |
| 2020/0230426 A1 | 7/2020 | Willis | |
| 2020/0238093 A1 | 7/2020 | Kim | |

FOREIGN PATENT DOCUMENTS

| | | | |
|---|---|---|---|
| JP | H06505662 A | 6/1994 | |
| JP | 2002538934 A | 11/2002 | |
| JP | 2003218805 A | 7/2003 | |
| JP | 2004512106 A | 4/2004 | |
| WO | 9725098 A1 | 7/1997 | |
| WO | 9961058 A1 | 12/1999 | |
| WO | 0176687 A2 | 10/2001 | |
| WO | 03070323 A1 | 8/2003 | |
| WO | 2004101062 A3 | 3/2004 | |
| WO | 2004089465 A1 | 10/2004 | |
| WO | 2004101062 A2 | 11/2004 | |
| WO | 2007149936 A2 | 12/2007 | |
| WO | 2008147703 A1 | 12/2008 | |
| WO | 2009120636 A1 | 10/2009 | |

OTHER PUBLICATIONS

U.S. Appl. No. 11/315,524, filed Dec. 21, 2005, Brisken.
U.S. Appl. No. 11/535,857, filed Sep. 27, 2006, Cowan.
Abraham et al., for the MIRACLE study group, "Cardiac Resynchronization in Chronic Heart Failure," N Engl J Med, 2002;346: 1845-53.
ACC/AHA Task Force on Practice Guidelines, "Evaluation and Management of Chronic Heart Failure in the Adult," JACC 2002; 38: 2101-13.
Allessie et al., "Regional Control of Atrial Fibrillation by Rapid Pacing in Conscious Dogs," Circulation 1991 ;84: 1689-97.
Ansalone et al., "Bi-ventricular pacing I heart failure: Back to basics in the pathophysiology of left bundle branch block to reduce the number of nonresponders," Am J Cardiol 2003;91 :55F-61F.
Auricchio eta l., "Cardiac resynchronization therapy: current state of the art," Circulation 2004; I 09:300-307.
Bardy et al., "The Totally Subcutaneous ICD System (The S-ICD)," PCAE. 2002, 24, 578.
Becker et al, "Suppression of Atrial Fibrillation by Multisite and Septal Pacing in a Novel Experimental Model", Cardiovascular Research 2001;54:476-481.
Bradley et al., "Cardiac Resynchronization and Death from Progressive Heart Failure: A Meta-Analysis of Randomized Controlled Trials," JAMA 2003;289:730-740.
Camm et al., Chapter 6: Nonpharmaceutical treatment of atrial fibrillation, In Atrial Fibrillation. Facts from Yesterday—Ideas for tomorrow. Future Publishing Company, Inc., Armonk, NY, 1994, pp. 125-147.
Dalecki et al., "Effects of Pulsed Ultrasound on the Frog Heart: I. Thresholds for Changes in Cardiac Rhythm and Aortic Pressure," Ultrasound in Med. & Biol. 1993; 19: 385-390.
Dalecki et al., "Effects of Pulsed Ultrasound on the Frog Heart: II. An Investigation of Heating as a Potential Mechanism," Ultrasound in Med. & Biol. 1993; 19: 391-398.
Dalecki et al., "Thresholds for premature ventricular contractions in frog hearts exposed to lithotripter fields," Ultrasound in Med. & Biol. 1991; 17:341-346.
Daoud et al., "Implantation Techniques and Chronic Lead Parameters of Biventricular Pacing Dual-chambers Defibrillators," J Cardiovasc Electrophysiology 2002; 13: 964-970.
Daubert et al., "Permanent Left Ventricular Pacing with Transvenous Leads Inserted Into the Coronary Veins," PACE 1998; 21: 239-245.
Daubert et al., "Use of Specifically Designed Coronary Sinus Leads for Permanent Left Ventricular Pacing: Preliminary Experience," PACE 1997; 20: II-NASPE Abstract 17, Apr. 1997.
David Trial Investigators, "The Dual Chamber and VVI Implantable Defibrillator (DAVID) Trial," JAMA 2002;288:3115-3123.
Deshmukh et al., "Direct His-bundle pacing: present and future," PACE 2004;27 [Pt.II]:862-70.
Ellenbogen et al., "Detection and Management of an Implantable Cardioverter Defibrillator Lead Failure," JACC 2003; 41: 73-80.
European Search Report and Search Opinion mailed Mar. 23, 2012 in European Patent Application No. 07841364.8.
European Search Report and Search Opinion mailed May 4, 2010 in European Patent Application No. 05855143, 8 pages.
Extended European Search Report mailed Mar. 26, 2008 in European Patent Application No. 05855395.9, 6 pages.
Feldman et al., "Comparison of medical therapy, resynchronization and defibrillation therapies in heart failure trial (COMPANION)," Presented at ACC 2003 Late Breaking Clinical Trials, 1 page.
Franz, "Mechano-electrical feedback in ventricular myocardium," Cardiovascular Research. 1996; 32: 15-24.
Gregoratos et al., ACC/AHA/NASPE 2002 guideline update for implantation of cardiac pacemakers and antiarrhythmia devices: a report of the American College of Cardiology/American Heart Association Task Force on Practice Guidelines (ACC/AHA/NASPE Committee to Update the 1998 Pacemaker Guidelines). Circulation. 2002; 106:2145-2161.
Hu et al., "Stretch-Activated Ion Channels in the Heart," J. Mol. Cell Cardiol. 1997; 29: 1511-1523.
International Search Report and Written Opinion mailed Apr. 7, 2008 in International Application No. PCT/US07/76812, 8 pages.
International Search Report and Written Opinion mailed Jun. 23, 2008 in International Application No. PCT/US05/46532, 8 pages.
Johnson et al., Adaptive Pacing during Ventricular Fibrillation, PACE 2003;26:1824-36.
Kalman J.M. et al, "Regional Entrainment of Atrial Fibrillation in Man", J Cardiovasc Electrophysiol 1991;7:867-76.

(56) References Cited

OTHER PUBLICATIONS

Kass et al., "Improved Left Ventricular Mechanics from Acute VDD Pacing in Patients with Dilated Cardiomyopathy and Ventricular Conduction Delay," Circulation 1999;99: 1567-73.
Kenknight B.H. et al., "Regional Capture of Fibrillating Ventricular Myocardium" Circ Res 1999;77:849-55.
Kohl et al., "Stretch-Induced Changes in Heart Rate and Rhythm: Clinical Observations, Experiments and Mathematical Models." Progress in Biophysics & Molecular Biology, 1999; 91: 91-138.
Kohl et al., "Sudden Cardiac Death by Commotio Cordis: Role of Merchano-Electrical Feedback," Cardiovascular Research, 2001; 50: 280-289.
Leclercq et al., "Acute Hemodynamic Effects of Biventricular DDD Pacing in Patients with End-Stage Heart Failure," JACC 1998; 32: 1825-1831.
Leclercq et al., "Systolic Improvement and Mechanical Resynchronization does not Require Electrical Synchrony in the Dilated Failing Heart with Left-Bundle-Branch Block," Circulation 2002; 106: 1760-1763.
Leclercq et al, "Is Dual Site Better than Single Site Atrial Pacing in the Prevention of Atrial Fibrillation?" PACE 2000;23"2102-7.
Lee et al., "Effect of Implantable Defibrillators of Arrhythmic Events and Mortality in the Multicenter Unsustained Tachycardia Trial," Circulation. 2002; 106: 233-238.
Linde et al., "Long-Term Benefits of Biventricular Pacing in Congestive Heart Failure: From the Multisite Stimulation in Cardiomyopathy (MUSTIC) Study," J Am Coll Cardiol 2002; 40: 111-118.
Miracle Trial Investigators, "Combined Cardiac Resynchronization and Implantable Cardioversion Defibrillation in Advanced Heart Failure:the Miracle ICD Trial," JAMA 2003; 289: 2685-2694.
Mirza et al., "Biatrial Pacing for Paroxysmal Atrial Fibrillation", J Am Coll Cardiol 2002;40:457-463.
Moss et al., "Prophylactic Implantation of a Defibrillator in Patients with Myocardial Infarction and Reduced Ejection Fraction," N Engl J Med. 2002; 346: 877-933.
Niehaus et al., "Non-Contact Cardiac Stimulation with locused Ultrasound Pulses," PACE 2003: 216: 1023.
Nielsen et al., "A Randomized Comparison of Atrial and Dual-Chambered Pacing in 177 Consecutive Patients with Sick Sinus Syndrome," J Am Coll Cardiol 2003; 42: 614-623.
Nolte et al., "Mechanically Induced Ventricular Extrasystoles in the Isolated Perfused Guinea-Pig Heart," Arzneim.—Forsch/drug Research. 1987; 37(11): 1025-1029.
Office Action dated Jan. 3, 2012 for U.S. Appl. No. 12/554,257.
Office Action dated May 14, 2012 for U.S. Appl. No. 12/554,257.
Office Action dated Jun. 23, 2008 for U.S. Appl. No. 11/535,857.
Office Action dated Sep. 14, 2010 for U.S. Appl. No. 12/554,234.
Office Action dated Nov. 12, 2008 for U.S. Appl. No. 11/535,857.
Peschar et al., "Left ventricular septal and apex pacing for optimal pump function in canine hearts," J Am Coll Cardiol 2003;41 :1218-26.
Reiter et al., "Effects of Mechano-Electrical Feedback: Potential Arrhythmogenic Influence in Patients with Congestive Heart Failure," Cardiovascular Research, 1996; 32: 44-51.
Smailys et al., "Investigation of the Possibilities of Cardiac Defibrillation by Ultrasound," Resuscitation, 1981; 9: 233-242.
Sowton., "Clinical Results with the Tachylog Antitachycardia Pacemaker", PACE 1984;7(Part 11):1313-1317.
Tacker, Chapter 1: Fibrillation causes and criteria for defibrillation. In Defibrillation of the Heart. Tacker, WA, ed. Mosby—Year Book, Inc., St. Louis, Missouri, 1994, pp. 1-14.
The Antiarrhythmics Versus Implantable Defibrillators (AVID) Investigators, "A Comparison of Antiarrhythmic Drug Therapy with Implantable Defibrillators in Patients Resuscitated from Near Fatal Ventricular Arrhythmias," N Engl J Med, 1997; 337: 1576-1583.
Valls-Bertault et al., "Adverse Events with Transvenous Left Ventricular Pacing in Patients with Severe Heart Failure: Early Experience from a Single Centre," Europace, 2001; 3: 60-63.
Warren et al., "Clinical Evaluation of Automatic Tachycardia Diagnosis by an Implanted Device", PACE 1986;9 (Part 11):1079-1083.

European Search Report and Search Opinion dated Oct. 4, 2011 for Application No. 09725046.8.
Examination Report mailed Feb. 25, 2013 in European Patent Application No. 08755507.4, 4 pages.
Extended Search Report in European Patent Application No. 08755507. 4, filed Jun. 7, 2010, 7 pages.
International search report and written opinion dated May 18, 2009 for PCT/US2009/037978.
International Search Report and Written Opinion mailed Jul. 17, 2008 in International Application No. PCT/US08/63669, 12 pages.
Marrouche, et al. Nonexcitatory stimulus delivery improves left ventricular function in hearts with left bundle branch block. J Carcovasc Electrophysiol. 2002; 13(7):691-695.
Mcpherson, et al. Seizing the Science of Ultrasound Beyond Imaging and Into Physiology and Therapeutics. Journal of the American College of Cardiology 2003;41: 1628-30.
Meltzer, et al. Therapeutic Cardiac Ultrasound. American Journal of Cardiology. 1991 ;67:422-4.
Miyamoto, et al. Coronary Vasodilation by Noninvasive Transcutaneous Ultrasound An In ivo Canine Study. Journal of the American College of Cardiology. 2003;41 :1623-7.
Mohri, et al. Cardiac Contractility Modulation by electric Currents Applied During the Refractory Period. Am J Physiol Heart Ciro Physiol. 2002;282:H1642-1647.
Mond. Selective Site Pacing: The Future of Cardiac Pacing? PACE 2004;27:835-836.
Mortimer, et al. Letter to the Editor: Altered Myocardial Contractility with Pulsed Ultrasound. Ultrasound in Med and Biol. 1987;13(9):L567-9.
Nishida, et al. Extracorporeal cardiac shock wave therapy markedly ameliorates ischemia-induced myocardial dysfunction in pigs in vivo. Circulation. 2004;110:3055-3061.
Non-Final Office Action mailed Aug. 31, 2011 in U.S. Appl. No. 11/752,775, 25 pages.
Non-Final Office Action mailed Aug. 7, 2009 in U.S. Appl. No. 11/752,775, 32 pages.
Non-Final Office Action mailed Dec. 13, 2018 in U.S. Appl. No. 16/107,626, 8 pages.
Non-Final Office Action mailed Jun. 10, 2013 in U.S. Appl. No. 11/752,775, 14 pages.
Non-Final Office Action mailed Oct. 22, 2015 in U.S. Appl. No. 14/221,040, 8 pages.
Non-Final Office Action mailed Sep. 19, 2017 in U.S. Appl. No. 14/221,040, 10 pages.
Notice of Allowance dated Oct. 25, 2017 for U.S. Appl. No. 15/043,210.
Notice of Allowance mailed Dec. 24, 2013 in U.S. Appl. No. 11/752,775, 8 pages.
Notice of Allowance mailed May 11, 2018 in U.S. Appl. No. 14/221,040, 9 pages.
Non-Final Office Action dated Jan. 12, 2017 for U.S. Appl. No. 15/043,210.
Final Office Action dated Feb. 12, 2013 for U.S. Appl. No. 12/890,308.
Final Office Action dated Mar. 23, 2015 for U.S. Appl. No. 12/890,308.
Non-Final Office Action dated May 27, 2014 for U.S. Appl. No. 12/890,308.
Non-Final Office Action dated Jul. 18, 2012 for U.S. Appl. No. 12/890,308.
Office Action dated Aug. 9, 2013 for Japanese Application No. 2010-509453, 5 pages with English translation.
Office Action dated Nov. 19, 2012 for Japanese Application No. 2010-509453, 7 pages with English translation.
Pappone, et al. Cardiac Contractility Modulation by electric currents applied during the refractory period in patients with heart failure secondary to ischemic or idiopathic dilated cardiomyopathy. Am J Cardiol 2002;90(12):1307-1313.
Pappone, et al. First Human Chronic Experience with Cardiac Contractility Modulation by Nonexcitatory Electrical Currents for Treating Systolic Heart Failure: Mid-Term Safety and Efficacy Results from a Multicenter Study. J Cardiovasc Electrophysiol 2004; 15:418-427.

(56) References Cited

OTHER PUBLICATIONS

Soykan. Automated Piecewise Linear Modeling of Pacing Leads. Engineering in Medicine and Biology Society, Engineering Advances: New Opportunities for Biomedical Engineers. Proceedings of the 16th Annual International Conference of the IEEE (Nov. 3-6, 1994); vol. 1, pp. 53-54.
Stix, et al. Chronic electrical stimulation during the absolute refractory period of the myocardium improves severe heart failure. European Heart J 2004;25:650-655.
Suchkova, et al. Ultrasound improves tissue perfusion in ischemic tissue through a nitric oxide-dependent mechanism. Throm Haemost. 2002;88:865-70.
Zakharov, et al. The action of Ultrasound On The Contraction Strength and Cation Potential of the Papillary Muscle of the Rat Heart. Biul Eksp Biol Med. Apr. 1989; 107(4):423-6.
Zakharov, et al. The Effect of Acoustic Cavitation on the Contraction Force and Membrane Potential of Rat Papillary Muscle. Ultrasound Med. Biol. 1989; 15 (6):561-5.
Final Office Action mailed Jun. 2, 2010 in U.S. Appl. No. 11/752,775, 20 pages.
Final Office Action mailed Jun. 30, 2016 in U.S. Appl. No. 14/221,040, 11 pages.
International Search Report and Written Opinion mailed May 12, 2023 in International Application No. PCT/US23/12534, 15 pages.

\* cited by examiner

TISSUE STIMULATION SYSTEMS AND METHODS, SUCH AS FOR PACING CARDIAC TISSUE

TECHNICAL FIELD

The present technology generally relates to implantable medical devices and, in particular embodiments, to leadless tissue stimulation systems and methods for pacing cardiac tissue.

BACKGROUND

Electrical stimulation of body tissue is used throughout medicine for treatment of both chronic and acute conditions. Among many examples, peripheral muscle stimulation is reported to accelerate healing of strains and tears, bone stimulation is likewise indicated to increase the rate of bone regrowth/repair in fractures, and nerve stimulation is used to alleviate chronic pain. Further there is encouraging research in the use of electrical stimulation to treat a variety of nerve and brain conditions, such as essential tremor, Parkinson's disease, migraine headaches, functional deficits due to stroke, and epileptic seizures.

Cardiac pacemakers and implantable defibrillators are examples of commonly implanted device utilizing electrical stimulation to stimulate cardiac and other tissues. A pacemaker is a battery-powered electronic device implanted under the skin, connected to the heart by an insulated metal lead wire with a tip electrode. Pacemakers were initially developed for and are most commonly used to treat slow heart rates (bradycardia), which may result from a number of conditions. More recently, advancements in pacemaker complexity, and associated sensing and pacing algorithms have allowed progress in using pacemakers for the treatment of other conditions, notably heart failure (HF) and fast heart rhythms (tachyarrhythmia/tachycardia).

Electrical energy sources connected to electrode/lead wire systems have typically been used to stimulate tissue within the body. The use of lead wires is associated with significant problems such as complications due to infection, lead failure, and electrode/lead dislodgement. The requirement for leads in order to accomplish stimulation also limits the number of accessible locations in the body. The requirement for leads has also limited the ability to stimulate at multiple sites (multisite stimulation).

BRIEF DESCRIPTION OF THE DRAWINGS

Many aspects of the present disclosure can be better understood with reference to the following drawings. The components in the drawings are not necessarily to scale. Instead, emphasis is placed on clearly illustrating the principles of the present disclosure.

DETAILED DESCRIPTION

Figure 1:
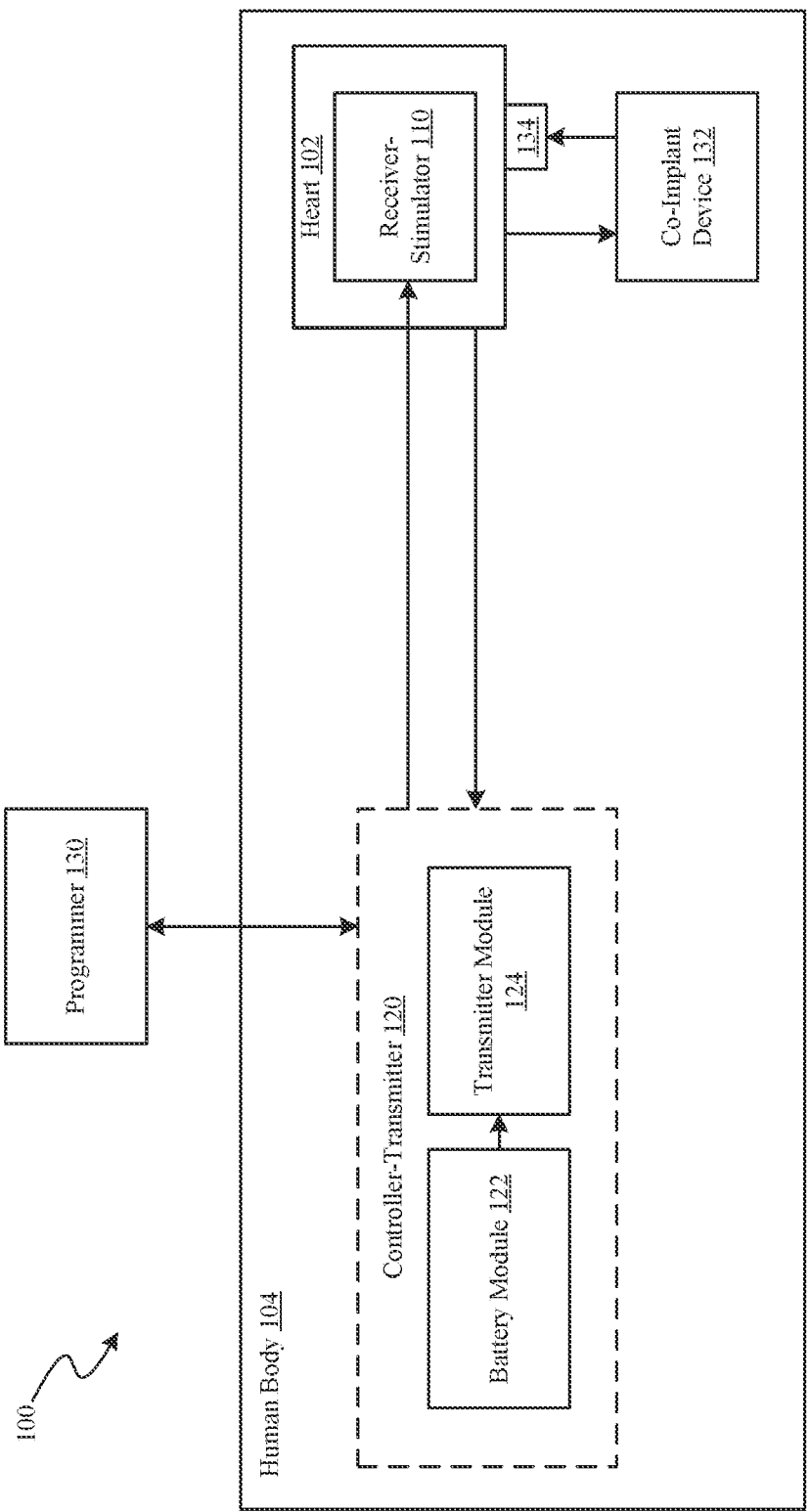
FIG. 1 is a schematic diagram of a tissue stimulation system configured in accordance with embodiments of the present technology.

Aspects of the present disclosure are directed generally to systems and methods for stimulating tissue of a patient, such as heart tissue for cardiac pacing. In several of the embodiments described below, for example, a system for stimulating (e.g., pacing) the heart of a patient includes a controller-transmitter and one or more receiver-stimulators in operable communication with one another. The receiver-stimulator can be implanted at the heart of the patient and the controller-transmitter can be implanted in the patient remote from the heart. The controller-transmitter can be configured to transmit acoustic signals to the receiver-stimulator including acoustic energy and modulated and/or encoded stimulation parameters. The receiver-stimulator can receive the acoustic signals and convert the acoustic signals to electrical energy for delivery to the heart via one or more stimulation electrodes according to the stimulation parameters. The receiver-stimulator can further be configured to transmit a radiofrequency signal to the controller-transmitter including information about sensed physiological parameters of the patient, status information, and the like. In some embodiments, the controller-transmitter can receive the radiofrequency signal and modify the transmitted acoustic signals accordingly. In some embodiments, the controller-transmitter can further transmit a radiofrequency signal to the receiver-stimulator, and the receiver-stimulator can harvest energy from the radiofrequency signal to power one or more electronic components thereof (e.g., a controller, a physiological sensor).

In several additional embodiments described below, a method of delivering electrical stimulation energy to the heart of a patient can include receiving a cardiac signal indicative of a function of the heart from, for example, the receiver-stimulator or the controller-transmitter. The method can further include determining a temporal spacing between a selected number of beats of the heart based on the received cardiac signal, and determining an average temporal spacing between the beats to determine a pacing pulse interval. The method can then include delivering the electrical stimulation to the heart according to the pacing pulse interval. In some aspects of the present technology, determining the temporal spacing does not include (e.g., is not dependent on) determining an amplitude or morphology of a waveform of the cardiac signal.

In several additional embodiments described below, an implanted receiver-stimulator includes a storage unit configured to store electrical energy converted from acoustic signals transmitted by a controller-transmitter. The storage unit can be electrically coupled to one or more stimulation electrodes via a switch. The receiver-stimulator can further include a controller electrically coupled to the switch and configured to control the switch to close and open one or more times to deliver the electrical energy from the storage unit to the stimulation electrodes for output to the heart as a first electrical pulse and a second electrical pulse. The controller-transmitter can be configured to detect the first electrical pulse and to cease transmission of the acoustic signal in response to detecting the first electrical pulse. In some embodiments, the controller can control the switch to deliver the first stimulation pulse based on a charge state of the storage unit such that, for example, the controller-transmitter ceases transmission of the acoustic signal when the storage unit is sufficiently charged. The second electrical pulse can have an amplitude, pulse duration, and/or other characteristic sufficient to stimulate the heart of the patient.

Specific details of several embodiments of the present technology are described herein with reference to FIGS. 1-8. The present technology, however, can be practiced without some of these specific details. In some instances, well-known structures and techniques often associated with leadless tissue stimulation systems, cardiac pacing, electronic circuitry, acoustic and radiofrequency transmission and receipt, and the like, have not been shown in detail so as not to obscure the present technology. The terminology used in the description presented below is intended to be interpreted in its broadest reasonable manner, even though it is being used in conjunction with a detailed description of certain specific embodiments of the disclosure. Certain terms can even be emphasized below; however, any terminology intended to be interpreted in any restricted manner will be overtly and specifically defined as such in this Detailed Description section.

The accompanying Figures depict embodiments of the present technology and are not intended to be limiting of its scope. The sizes of various depicted elements are not necessarily drawn to scale, and these various elements can be arbitrarily enlarged to improve legibility. Component details can be abstracted in the Figures to exclude details such as position of components and certain precise connections between such components when such details are unnecessary for a complete understanding of how to make and use the present technology. Many of the details, dimensions, angles, and other features shown in the Figures are merely illustrative of particular embodiments of the disclosure. Accordingly, other embodiments can have other details, dimensions, angles, and features without departing from the spirit or scope of the present technology.

General aspects of the systems and methods of the present technology, and the environments in which the present technology can operate, are described below with reference to FIG. 1. Further embodiments of the technology are described below with reference to FIGS. 2-8. One of ordinary skill in the art will appreciate that the components and functionalities of the various embodiments can be combined with one another. For example, any of the receiver-stimulators and/or controller-transmitters and associated methods described in detail with reference to FIGS. 2-8 can be combined with one another and/or operate in the environments described with reference to FIG. 1. Moreover, while the present technology is generally described in the environment of stimulating the heart, one of ordinary skill in the art will understand that one or more aspects of the present technology are applicable to other implantable devices configured to treat other areas of the human body.

FIG. 1 is a schematic diagram of a tissue stimulation system 100 ("system 100") configured in accordance with embodiments of the present technology. In the illustrated embodiment, the system 100 is configured to stimulate a heart 102 within a body 104 of a human patient. The system 100 can include a receiver-stimulator 110 (which can also be referred to as a stimulator, ultrasound receiver, an acoustic receiver, and the like) in operable communication (e.g., wireless and/or radio communication) with a controller-transmitter 120 (which can also be referred to as an ultrasound transmitter, a pulse generator, an acoustic transmitter, and the like). The controller-transmitter 120 can include a battery module 122 and a transmitter module 124 operably coupled to and powered via the battery module 122. In some embodiments, both the receiver-stimulator 110 and the controller-transmitter 120 can be implanted within the body 104 of the human patient. For example, the receiver-stimulator 110 can be implanted at and/or proximate the heart 102 (e.g., in the left ventricle, the right ventricle, or proximate area) for delivering stimulation pulses to the heart 102, while the controller-transmitter 120 can be positioned at another location remote from the heart 102 (e.g., in the chest area). As described in greater detail below with reference to FIGS. 2-8, the transmitter module 124 of the controller-transmitter 120 can direct energy (e.g., acoustic energy, ultrasound energy) toward the receiver-stimulator 110, which can receive the energy and deliver one or more electrical pulses (e.g., stimulation pulses, pacing pulses) to the heart 102.

In some embodiments, the system 100 can further include a programmer 130 in operable communication with the controller-transmitter 120. The programmer 130 can be positioned outside the body 104 and operable to program (e.g., by a physician) various parameters of the controller-transmitter 120 and/or to receive diagnostic information from the controller-transmitter 120. In some embodiments, the system 100 can further include a co-implant device 132 (e.g., an implantable cardioverter defibrillator (ICD) or pacemaker) coupled to pacing leads 134 for delivering stimulation pulses to one or more portions of the heart 102 other than the area stimulated by the receiver-stimulator 110. In other embodiments, the co-implant device 132 can be a leadless pacemaker which is implanted directly into the heart to eliminate the need for separate pacing leads 134. The co-implant device 132 and the controller-transmitter 120 can operate in tandem and deliver stimulation signals to the heart 102 to cause a synchronized heartbeat. In some embodiments, the controller-transmitter 120 can receive signals (e.g., electrocardiogram signals) from the heart 102 to determine information related to the heart 102, such as a heart rate, heart rhythm, including the output of the pacing leads 134 located in the heart 102. In some embodiments, as described in greater detail below with reference to FIGS. 2-8, the controller-transmitter 120 can alternatively or additionally be configured to receive information (e.g., diagnostic signals) from the receiver-stimulator 110. The received signals can be used to adjust the ultrasound energy signals delivered to the receiver-stimulator 110.

The receiver-stimulator 110, the controller-transmitter 120, and/or the programmer 130 can include a machine-readable (e.g., computer-readable) or controller-readable medium containing instructions for generating, transmitting, and/or receiving suitable signals (e.g., stimulation signals, diagnostic signals). The receiver-stimulator 110, the controller-transmitter 120, and/or the programmer 130 can include one or more processor(s), memory unit(s), and/or input/output device(s). Accordingly, the process of providing stimulation signals and/or executing other associated functions can be performed by computer-executable instructions contained by, on, or in computer-readable media located at the receiver-stimulator 110, the controller-transmitter 120, and/or the programmer 130. Further, the receiver-stimulator 110, the controller-transmitter 120, and/or the programmer 130 can include dedicated hardware, firmware, and/or software for executing computer-executable instructions that, when executed, perform any one or more methods, processes, and/or sub-processes described herein. The dedicated hardware, firmware, and/or software also serve as "means for" performing the methods, processes, and/or sub-processes described herein.

In some embodiments, the system 100 can include several features generally similar or identical to those of the leadless tissue stimulation systems disclosed in (i) U.S. Pat. No. 7,610,092, filed Dec. 21, 2005, and titled "LEADLESS TISSUE STIMULATION SYSTEMS AND METHODS," (ii) U.S. Pat. No. 8,315,701, filed Sep. 4, 2009, and titled "LEADLESS TISSUE STIMULATION SYSTEMS AND METHODS," and/or (iii) U.S. Pat. No. 8,718,773, filed May 23, 2007, and titled "OPTIMIZING ENERGY TRANSMISSION IN A LEADLESS TISSUE STIMULATION SYSTEM."

Figure 2:
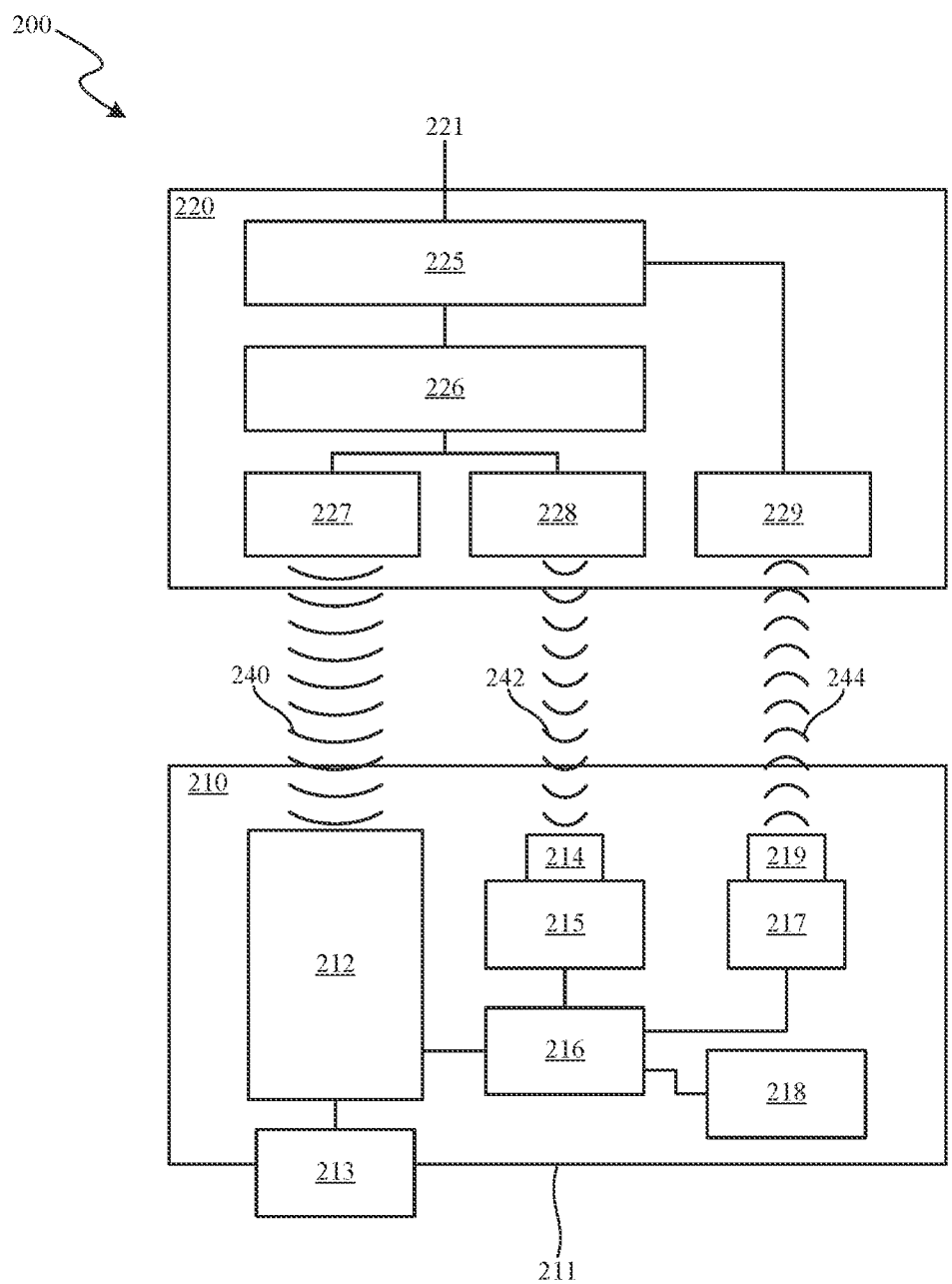
FIG. 2 is a schematic diagram of a tissue stimulation system configured in accordance with additional embodiments of the present technology.

FIG. 2 is a schematic diagram of a leadless tissue stimulation system 200 ("system 200") configured in accordance with embodiments of the present technology. The system 200 can include several features generally similar or identical to the features of the system 100 described in detail above with reference to FIG. 1. For example, the system 200 can include a receiver-stimulator 210 in operable communication with a controller-transmitter 220.

In the illustrated embodiment, the controller-transmitter 220 includes a signal conditioning and processing circuit 225, a controller 226 (e.g., control and timing circuitry, a communications module, a voltage regulator), a first communication circuit 227, second communication circuit 228, and a receiving circuit 229. In some embodiments, the signal conditioning and processing circuit 225 can receive signals from the receiving circuit 229 and/or signals from one more additional sources 221 and condition and/or process these signals before passing them to the controller 226. In some embodiments, the additional sources 221 can include an external programmer, such as the programmer 130 of FIG. 1. Moreover, as described in detail below with reference to FIG. 5, in some embodiments the signals from the additional source(s) 221 can include signals (e.g., pacing signals) from a co-implant device and/or physiological signals from one or more physiological sensors in and/or carried by the controller-transmitter 220. The controller 226 can use the information received from the signal conditioning and processing circuit 225 to generate (i) first control signals for the first communication circuit 227 to produce a first signal 240 for transmission to the receiver-stimulator 210 and/or (ii) second control signals for the second communication circuit 228 to produce a second signal 242 for transmission to the receiver-stimulator 210.

In some embodiments, the first signal 240 can be an ultrasound energy signal (e.g., an ultrasound energy transmission) having a particular frequency range such as for example, 500 kHz to 10 MHz, 800 kHz to 2 MHz, or 900 kHz to 1 MHz (e.g., about 921 kHz). The controller-transmitter 220 can transmit the first signal 240 as a focused beam of wireless energy (e.g., ultrasound energy). Accordingly, the first communication circuit 227 can comprise one or more transducers, signal generators, amplifiers, and the like for generating the first signal 240 and directing the first signal 240 toward the receiver-stimulator 210. In some embodiments, the second signal 242 is an electromagnetic signal having a frequency greater than a frequency of the first signal 240. For example, the second signal 242 can be a radiofrequency (RF) signal having a frequency of greater than 1 MHz, greater than 10 MHz, greater than 100 MHz, greater than 400 MHz, or greater. In a particular embodiment, the second signal 242 has a frequency of about 402-405 MHz. Accordingly, the second communication circuit 228 can comprise one or more signal generators, amplifiers, antennas, and the like for generating the second signal 242 and directing the second signal 242 toward the receiver-stimulator 210. Thus, in some aspects of the present technology the system 200 is a dual-frequency system operating at both an acoustic (e.g., ultrasound) frequency and a radiofrequency.

In general, the receiver-stimulator 210 includes a housing 211 containing and/or carrying various electronic components, circuit components, circuit blocks, functional blocks, and the like, that collectively enable the receiver-stimulator 210 to (i) receive the first signal 240 and the second signal 242 from the controller-transmitter 220, (ii) transmit a third signal 244 to the controller-transmitter 220, and (iii) deliver one or more electrical pulses (e.g., pacing pulses, stimulation pulses) to tissue of a patient (e.g., the heart 102 shown in FIG. 1). More specifically, in the illustrated embodiment the receiver-stimulator 210 includes a transducer-pacing circuit 212 that receives the first signal 240 and converts the first signal 240 into an electrical pacing pulse for delivery via one or more electrodes 213 (e.g., a pair of stimulation electrodes). In some embodiments, the transducer-pacing circuit 212 includes one or more piezoelectric elements (e.g., including crystal, ceramic, and/or other materials) that accumulate electrical charge in response to receiving the first signal 240, and circuitry (e.g., detector circuitry, envelope detector circuitry, rectifier circuitry, filtering circuitry, voltage-limiting circuitry) for producing a voltage pulse with an amplitude and length proportional to the first signal 240. The transducer-pacing circuit 212 can deliver the voltage pulse to the electrodes 213, which can project past and/or be incorporated into an outer surface of the housing 211 so as to contact the tissue of the patient when the receiver-stimulator 210 is in implanted therein. In some embodiments, the housing 211 comprises a hermetically sealed case of biologically compatible material.

In the illustrated embodiment, the receiver-stimulator 210 further includes a first antenna 214 that can receive the second signal 242 from the controller-transmitter 220, convert the second signal 242 to an electrical signal, and pass the electric signal to an energy-harvesting circuit 215. In the illustrated embodiment, the receiver-stimulator 210 further includes a communication circuit 217 and a physiological sensor 218 (e.g., a cardiac sensor) electrically coupled to a controller 216 (e.g., a processor, a voltage regulator). The energy-harvesting circuit 215 produces power (e.g., harvests energy) from the second signal 242 and passes that power to the controller 216. In some embodiments, the energy-harvesting circuit 215, the controller 216, the communication circuit 217, and/or another component (e.g., a capacitor, a battery) of the receiver-stimulator 210 can store the energy produced by the energy-harvesting circuit 215. The physiological sensor 218 can sense one or more intrinsic cardiac parameters of the heart of the patient (e.g., the heart 102 of FIG. 1) at which the receiver-stimulator 210 is implanted. For example, the physiological sensor 218 can comprise an intracardiac electrogram (IEGM) sensor and, in some embodiments, can measure the IEGM at the electrodes 213. In some embodiments, the physiological sensor 218 can additionally or alternatively include a transducer (e.g., a low frequency transducer, a microphone) that detects one or more cardiac sounds, such as sounds corresponding to the operation of a heart valve (e.g., an aortic valve, a mitral valve). Similarly, the physiological sensor 218 can detect the onset of certain cardiac events such as diastole, systole, and so on.

The communication circuit 217 can be electrically coupled to a second antenna 219 and can generate and/or pass electrical signals to the second antenna 219 for transmission to the controller-transmitter 220 (e.g., to the receiving circuit 229) as the third signal 244. In some embodiments, the communication circuit 217 performs pulse width modulation of signals from the controller 216 (and/or other components of the receiver-stimulator 210) at radiofrequency. In some embodiments, the third signal 244 has a frequency that is the same as or generally similar to the frequency of the second signal 242 (e.g., a RF-signal having a frequency of about 402-405 MHz). The communication circuit 217 and the second antenna 219 can be configured (e.g., shaped, positioned, tuned) to transmit the third signal 244 toward the controller-transmitter 220 as a focused beam of wireless energy. In some embodiments, the first and second antennas 214, 219 comprise multiple windings of a metal wire material (e.g., gold).

In some embodiments, the controller 216 can be an application-specific integrated circuit (ASIC) or other type of controller configured to at least partially control operation of the various electronic components of the receiver-stimulator 210. For example, the controller 216 can receive the power produced by the energy-harvesting circuit 215 and the physiological parameters detected by the physiological sensor 218 and send control signals to the communication circuit 217 to produce the third signal 244 for transmission to the controller-transmitter 220 including encoded information about the physiological parameters. That is, the controller 216 can utilize the power transferred via the second signal 242 to generate and transmit the third signal 244 (e.g., via the communication circuit 217 and second antenna 219) back to the controller-transmitter 220 including information about detected physiological parameters in real-time or near real-time. The receiving circuit 229 of the controller-transmitter 220 can include an antenna and/or other components for receiving and decoding the third signal 244 before passing the third signal 244 to, for example, the signal conditioning and processing circuit 225 and the controller 226. In some embodiments, the powered signal can additionally or alternatively include information about a status of the receiver-stimulator 210, an efficiency of pacing stimulation via the electrodes 213, and/or other information detected by the receiver-stimulator 210. The controller-transmitter 220 can utilize the information received via the third signal 244 to modify the first signal 240—such as a timing, amplitude, pulse length, and/or other characteristic of the first signal 240—to thereby control the electrical stimulation (e.g., pacing stimulation) output by the electrodes 213.

The power produced by the energy-harvesting circuit 215 can alternatively or additionally be used to provide stimulation pulses to the tissue of the patient via the electrodes 213. For example, in some embodiments the controller 216 can combine and/or manage the power received from the first signal 240 and the second signal 242 and provide an appropriate stimulation pulse or plurality of stimulation pulses to the electrodes 213 (e.g., via the transducer-pacing circuit 212). In some embodiments, power from the second signal 242 can be used as a backup power source for powering the electrodes 213 in the event the first signal 240 is lost. In some embodiments, power from the second signal 242 can be used to power the physiological sensor 218 and/or other electronic components of the receiver-stimulator 210.

Figure 3:
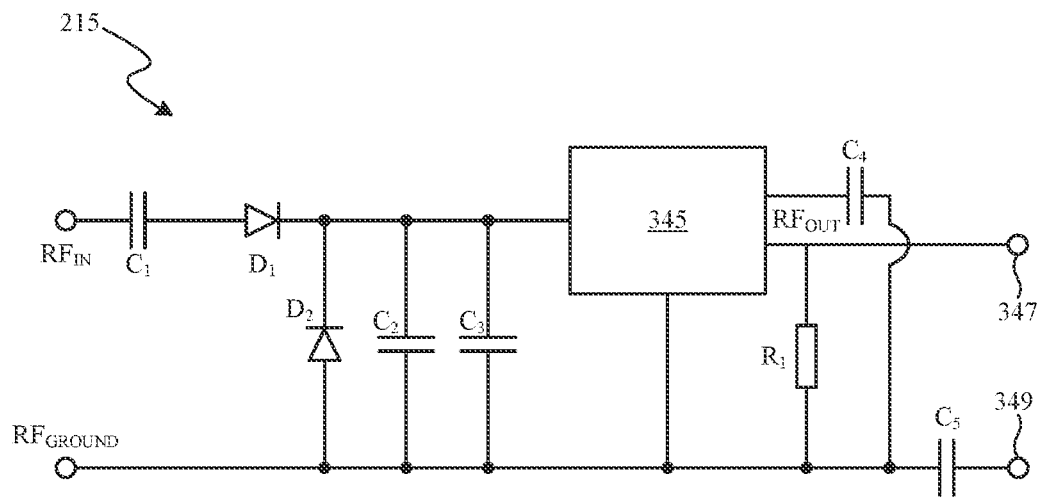
FIG. 3 illustrates an energy-harvesting circuit of a receiver-stimulator of the system of FIG. 2 configured in accordance with embodiments of the present technology.

FIG. 3 illustrates the energy-harvesting circuit 215 of the receiver-stimulator 210 shown in FIG. 2 configured in accordance with embodiments of the present technology. Referring to FIGS. 2 and 3 together, the energy-harvesting circuit 215 can harvest energy from the second signal 242 (e.g., a radiofrequency signal) transmitted from the controller-transmitter 220 to the receiver-stimulator 210. After receiving the second signal 242 through the first antenna 214, the first antenna 214 passes a radiofrequency input signal $RF_{IN}$ to the energy-harvesting circuit 215. As shown in FIG. 3, the energy-harvesting circuit 215 includes electrical connectors for receiving the input signal $RF_{IN}$ and a ground signal $RF_{GROUND}$. The input signal $RF_{IN}$ can be passed through a first diode $D_1$ and a second diode $D_2$ to rectify the input signal $RF_{IN}$. In some embodiments, the first and second diodes $D_1$ and $D_2$ can be Schottky diodes, which have a low forward voltage for energy efficiency. In the illustrated embodiment, the energy-harvesting circuit 215 further includes a network of capacitors C (including individually identified first through fifth capacitors $C_1$-$C_5$, respectively). The first through third capacitors $C_1$-$C_3$ can be connected across the input signal $RF_{IN}$ to provide a selected capacitance for signal conditioning before the rectified and conditioned input signal $RF_{IN}$ is input into a charge pump 345. In some embodiments, the charge pump 345 can be of the type sold by Seiko Instruments Inc., under the product model "S882Z." In other embodiments, the charge pump 345 can be another type of charge pump and/or can be integrated into the controller 216 (FIG. 2).

In the illustrated embodiment, the charge pump outputs an output signal $RF_{OUT}$ that can be further conditioned via a resistor R1 (e.g., a high value resistor (HVR)), the fourth capacitor $C_4$, and/or the fifth capacitor $C_5$. Referring to FIGS. 2 and 3 together, the conditioned output signal $RF_{OUT}$ can be output to the controller 216 (e.g., a voltage regulation circuit of the controller 216) via an anode 347 and a cathode 349. In other embodiments, the energy-harvesting circuit 215 can include more or fewer electronic components suitable for harvesting the energy from the second signal 242 and outputting the energy (e.g., a voltage) to the controller 216 and/or another component of the receiver-stimulator 210.

Figure 4:
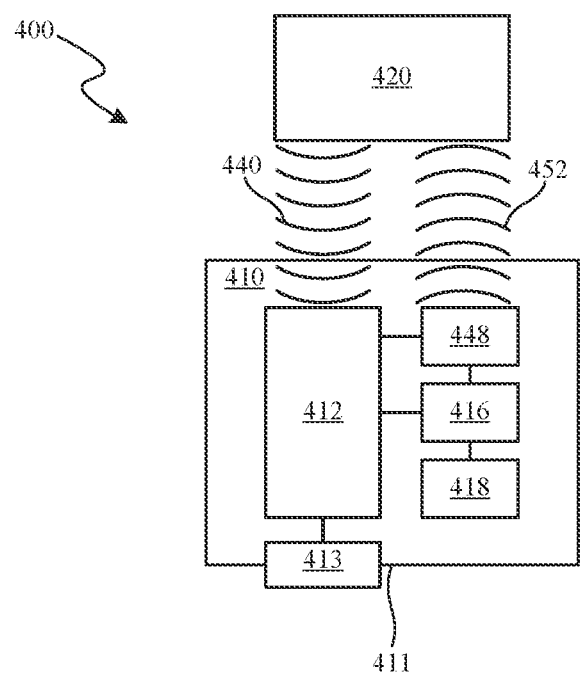
FIG. 4 is a schematic diagram of a tissue stimulation system configured in accordance with additional embodiments of the present technology.

FIG. 4 is a schematic diagram of a tissue stimulation system 400 ("system 400") configured in accordance with embodiments of the present technology. The system 400 can include several features generally similar or identical to the features of the systems 100 and/or 200 described in detail above with reference to FIGS. 1-3. For example, the system 400 can include a receiver-stimulator 410 in operable communication with a controller-transmitter 420. Likewise, in the illustrated embodiment the receiver-stimulator 410 includes a housing 411 containing and/or carrying a transducer-pacing circuit 412, stimulation electrodes 413, a controller 416 (e.g., a voltage-regulating ASIC), and a physiological sensor 418. The transducer-pacing circuit 412 can receive a first signal 440 (e.g., an acoustic ultrasound signal) from the controller-transmitter 420 and convert the first signal 440 into an electrical pacing pulse for delivery via one or more of the electrodes 413.

In the illustrated embodiment, the receiver-stimulator 410 further includes a communication circuit 448 electrically coupled to the transducer-pacing circuit 412 and/or the controller 416. The communication circuit 448 can receive a portion of the first signal 440 and encode and/or modulate the portion of the first signal 440 with information from the physiological sensor 418 and/or status information about the receiver-stimulator 410 for transmission back to the controller-transmitter 420 as a second signal 452. In some embodiments, the communication circuit 448 is configured to encode the information into the second signal 452 using pulse position and/or pulse width codes. In some embodiments, the first and second signals 440, 452 can be acoustic signals (e.g., ultrasound signals) having the same or substantially similar frequency such as, for example, between about 500 kHz to 10 MHz, 800 kHz to 2 MHz, or 900 kHz to 1 MHz (e.g., about 921 kHz). Therefore, the communication circuit 448 can include one or more transducer elements (e.g., piezoelectric elements), antennas, and/or modulation components configured to generate the second signal 452 and direct the second signal 452 toward the controller-transmitter 420 (e.g., an ultrasound receiver therein) as a focused beam of ultrasound energy. Accordingly, in some aspects of the present technology the system 400 is a single-frequency system operating to both receive the first signal 440 at and transmit the second signal 452 from the receiver-stimulator 410 at the same or substantially similar frequency.

In other embodiments, the communication circuit 448 can comprise a speaker or piezoelectric beeper that can transmit the second signal 452 as audible sounds toward the controller-transmitter 420. In such embodiments, the controller-transmitter 420 can include a microphone for receiving the second signal 452 and converting the second signal 452 to an electric signal.

Figure 5:
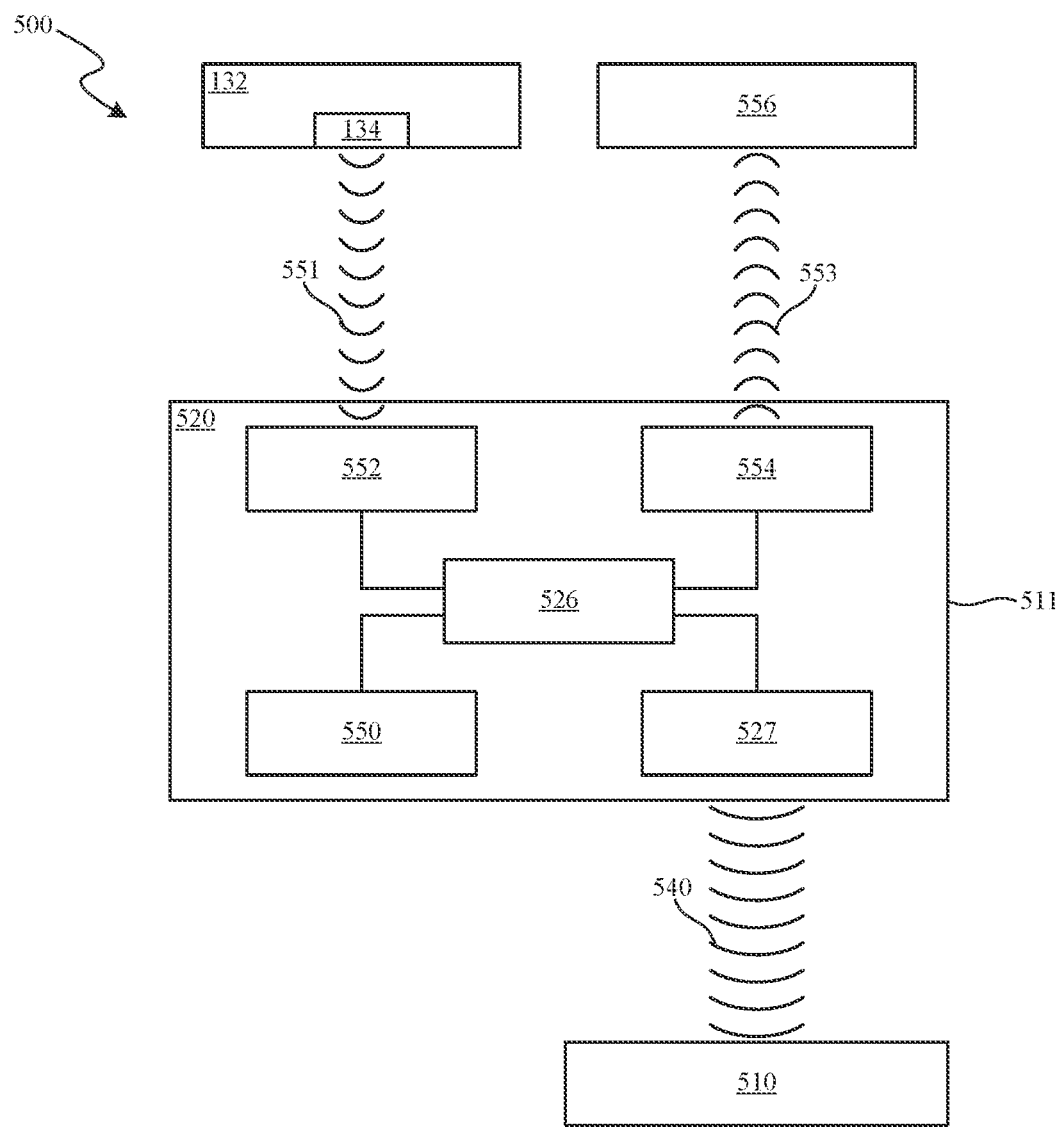
FIG. 5 is a is a schematic diagram of a tissue stimulation system configured in accordance with additional embodiments of the present technology

FIG. 5 is a is a schematic diagram of a tissue stimulation system 500 ("system 500") configured in accordance with embodiments of the present technology. The system 500 can include several features generally similar or identical to the features of the systems 100, 200, and/or 400 described in detail above with reference to FIGS. 1-4. For example, the system 500 can include a receiver-stimulator 510 in operable communication with a controller-transmitter 520. The controller-transmitter 520 can include a controller 526 electrically coupled to a first communication circuit 527 and configured to generate first control signals for the first communication circuit 527 to produce a first signal 540 (e.g., an acoustic ultrasound signal) for transmission to the receiver-stimulator 510. The receiver-stimulator 510 can receive the first signal 540 and output an electrical stimulation pattern based on the first signal 540.

In the illustrated embodiment, the controller-transmitter 520 further includes a physiological sensor 550 that can, for example, sense one or more intrinsic cardiac parameters of a heart of a patient (e.g., the heart 102 of FIG. 1). In some embodiments, the physiological sensor 550 can include one or more electrodes positioned on a casing 511 of the controller-transmitter 520 (e.g., on an exterior or outer surface of the casing 511 facing the heart) for sensing a far-field electrogram (EGM), an impedance, plethysmography information, and/or hemodynamic activity. In additional embodiments, the physiological sensor 550 can be an optical sensor (e.g., a photoplethysmography (PPG) optical sensor), a microphone configured to detect one or more cardiac sounds such as mitral and/or aortic valve heart sounds, and/or another type of sensor. After detecting the one or more physiological parameters, the physiological sensor 550 can pass a signal representative of the parameters to the controller 526 and/or another electronic component of the controller-transmitter 520.

In the illustrated embodiment, the controller-transmitter 520 further includes a receiving circuit 552 that can receive a second signal 551 from a co-implant device (e.g., the co-implant device 132 of FIG. 1). The second signal 551 can include instructions for programming parameters (e.g., operational parameters) of the controller-transmitter 520 to trigger a specific output of the first signal 540. In some embodiments, the second signal 551 is a radiofrequency signal and the receiving circuit 552 can include an antenna and/or other components for receiving and decoding the second signal 551. Accordingly, the second signal 551 can be a wireless radiofrequency communication signal. In other embodiments, the second signal 551 can be an electrical signal (e.g., an electrical pulse) generated by the pacing leads 134 of the co-implant device 132 and/or other electrodes of the co-implant device 132 such as, for example, dedicated communication electrodes positioned on an external surface of the co-implant device 132. In other embodiments, the controller-transmitter 520 can be communicatively coupled to the co-implant device 132 via a different wireless or wired communication link. After receiving, decoding, and/or processing the second signal 551, the receiving circuit 552 can pass the second signal 551 to the controller 526 and/or another electronic component of the controller-transmitter 520.

The controller 526 is electrically coupled to the physiological sensor 550 and the receiving circuit 552 and can generate the first control signals for generating the first signal 540 based at least in part on (i) the physiological parameters detected by the physiological sensor 550 and/or (ii) the instructions transmitted by the co-implant device 132. That is, the controller 526 can cause the first communication circuit 527 to generate and transmit the first signal 540 in accordance with sensed physiological parameters of the patient and/or instructions from the co-implant device 132 to, for example, cause the receiver-stimulator 510 to produce a specific stimulation output. In some embodiments, the controller-transmitter 520 can be configured as a "slave" to the "master" co-implant device 132 such that the parameters (e.g., amplitude, timing, pulse characteristics) of the first signal 540 are driven only or substantially only by the instructions of the co-implant device 132 communicated via the second signal 551.

In the illustrated embodiment, the controller-transmitter 520 further includes a second communication circuit 554 operably coupled to the controller 526. The controller 526 can generate second control signals for the second communication circuit 554 to produce a third signal 553 for transmission to an external device 556, such as a smartphone, tablet, computer, or other electronic device. In some embodiments, the third signal 553 is a Bluetooth signal (e.g., a Bluetooth Low Energy (BLE) signal) that communicatively couples the controller-transmitter 520 to the external device 556. Accordingly, the second communication circuit 554 can comprise a Bluetooth chip including a Bluetooth antenna, amplifier, and/or other electronic components. In some embodiments, the controller 526 can operate the second communication circuit 554 to communicate data from the physiological sensor 550, data from the co-implant device 132, status information, and/or other information to the external device 556 via the third signal 553. In some embodiments, the external device 556 can be a device of a physician of the patient such that information can be automatically communicated from the system 500 to the physician without the intervention of the patient.

Figure 6:
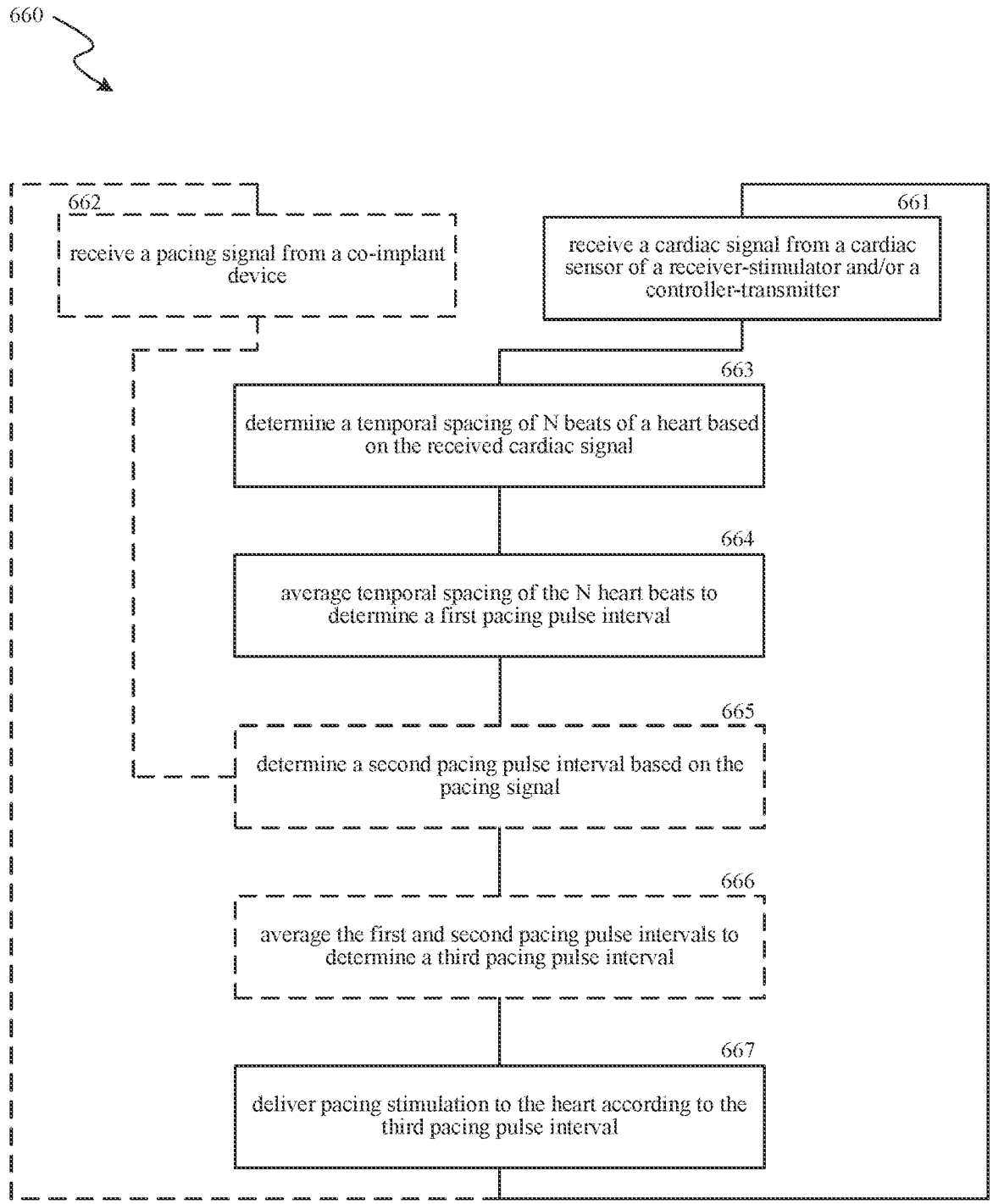
FIG. 6 is a flow diagram of a process or method for a tissue stimulation system to generate and deliver electrical stimulation (e.g., electrical pacing pulses) to the heart of a patient in accordance with embodiments of the present technology.

FIG. 6 is a flow diagram of a process or method 660 for using a tissue stimulation system to generate and deliver electrical stimulation (e.g., electrical pacing pulses) to the heart of a patient in accordance with embodiments of the present technology. Although some features of method 660 are described in the context of the embodiments described in detail with reference to FIGS. 1-5, one skilled in the art will readily understand that the method 660 can be carried out using other suitable systems and/or devices described herein.

At block 661, the method 660 includes receiving a cardiac signal from a cardiac sensor of a receiver-stimulator implanted at the heart and/or a controller-transmitter implanted in the patient remote from the heart. For example, in some embodiments the controller 226 of the controller-transmitter 220 can wirelessly receive the cardiac signal 244 from the physiological sensor 218 of the receiver-stimulator 210, and/or receive the cardiac signal 452 from the physiological sensor 418 of the receiver-stimulator 410. In other embodiments, the physiological sensor 550 of the receiver-stimulator 510 can directly detect the cardiac signal. The cardiac signal can include EGM information, plethysmography information, audio information, and/or other cardiac information.

Optionally, at block 662, the method 660 can include receiving a pacing signal from a co-implant device. For example, in some embodiments the controller-transmitter 520 can directly receive the pacing signal 551 from the co-implant device 132 over a wireless communication link or can detect the pacing signal via, for example, one or more electrodes of the controller-transmitter 520.

At block 663, the method 660 includes determining, based on the received cardiac signal, a temporal spacing of a predetermined number (N) beats of the heart. In general, this determination is based on the specific type of cardiac signal received from the cardiac sensor. For example, where the cardiac signal is an ECG signal (e.g., recorded at the controller-transmitter or recorded at the receiver-stimulator and wirelessly transmitted to controller-transmitter), the block 663 can include detecting a temporal spacing between one or more of a P-wave (e.g., representing atrial depolarization), a QRS-segment (e.g., representing ventricular depolarization), a T-wave (e.g., representing ventricular repolarization), and/or other features in the ECG waveform in successive heart beats. Similarly, where the cardiac signal is a plethysmography signal, the block 663 can include detecting a temporal spacing between spikes in the plethysmography waveform representing blood volume (e.g., a minimum or maximum blood volume) in successive heart beats. Likewise, where the cardiac signal comprises audio information about heart function (e.g., heart valve opening and/or closing), the block 663 can include detecting a temporal spacing between features in the audio waveform representing the opening and closing of heart valves, the contraction and expansion of the atria and/or ventricles, and so on, in successive heart beats. In some embodiments, the cardiac signal can be processed (e.g., filtered) to better facilitate determination of the temporal spacing between heart beats.

At block 664 the method 660 includes averaging the temporal spacing of the N heart beats to determine a first pacing pulse interval by, for example, dividing the temporal spacing by N. For example, where the temporal spacing between 10 heart beats (i.e., N=10) is determined at block 663, the block 664 can include dividing the total time elapsed between the first detected heart beat and the tenth detected heart beat by 10 to determine the first pacing pulse interval. In some embodiments, the number of heart beats N can be two, between two to ten, ten, or greater than ten.

At block 665, the method 660 can optionally include determining a second pacing pulse interval based on the pacing signal optionally received at block 662. In general, this determination is based on the specific type of pacing signal received from the cardiac sensor. For example, where the co-implant device 132 directly transmits information (e.g., the second signal 551) to the controller-transmitter 520 (e.g., over a RF communication link), the transmitted information can include the second pacing pulse interval. Where the controller-transmitter directly detects the pacing signal of the co-implant device 132 (e.g., via one or more electrodes), determining the second pacing pulse interval can include determining a temporal spacing between features (e.g., electrical spikes) representing successive heart beats and averaging over the number of heart beats (e.g., similar to the methodology of blocks 663 and 664).

At block 666, the method 660 can optionally include averaging the first and second pacing pulse intervals to determine a third pacing pulse interval. At block 667, the method can include delivering pacing stimulation to the heart according to the third pacing pulse interval, or according to the first pacing pulse interval if the second pacing pulse interval is not detected (i.e., in the omission of optional blocks 662, 665, and/or 666). For example, the controller 226 can send control signals to the first communication circuit 227 to produce the first signal 240 according the determined third pacing pulse interval (e.g., with the third pacing pulse interval encoded therein). The transducer-pacing circuit 212 can receive the first signal 240 and convert the first signal 240 to an electrical pacing output that is delivered via the electrodes 213 according to the third pacing interval.

Accordingly, in some aspects of the present technology the method 660 can help ensure that the electrodes 213 deliver pacing stimulation at specifically selected times relative to the heart beat of the patient. For example, in some embodiments the pacing stimulation can be reliably applied slightly ahead of ventricular depolarization (e.g., the QRS-segment of the ECG). Moreover, the method 660 is not dependent upon the morphologies or amplitudes of the cardiac signal, but rather on the temporal characteristics of the cardiac signal.

In some embodiments, the method 660 can return to blocks 661 and/or 662. For example, the method 660 can include delivering pacing stimulation (the block 667) for a predetermined amount of time and/or a predetermined number of heart beats before the method 660 returns to blocks 661 and/or 662 to recalibrate the pacing pulse interval.

Figure 7:
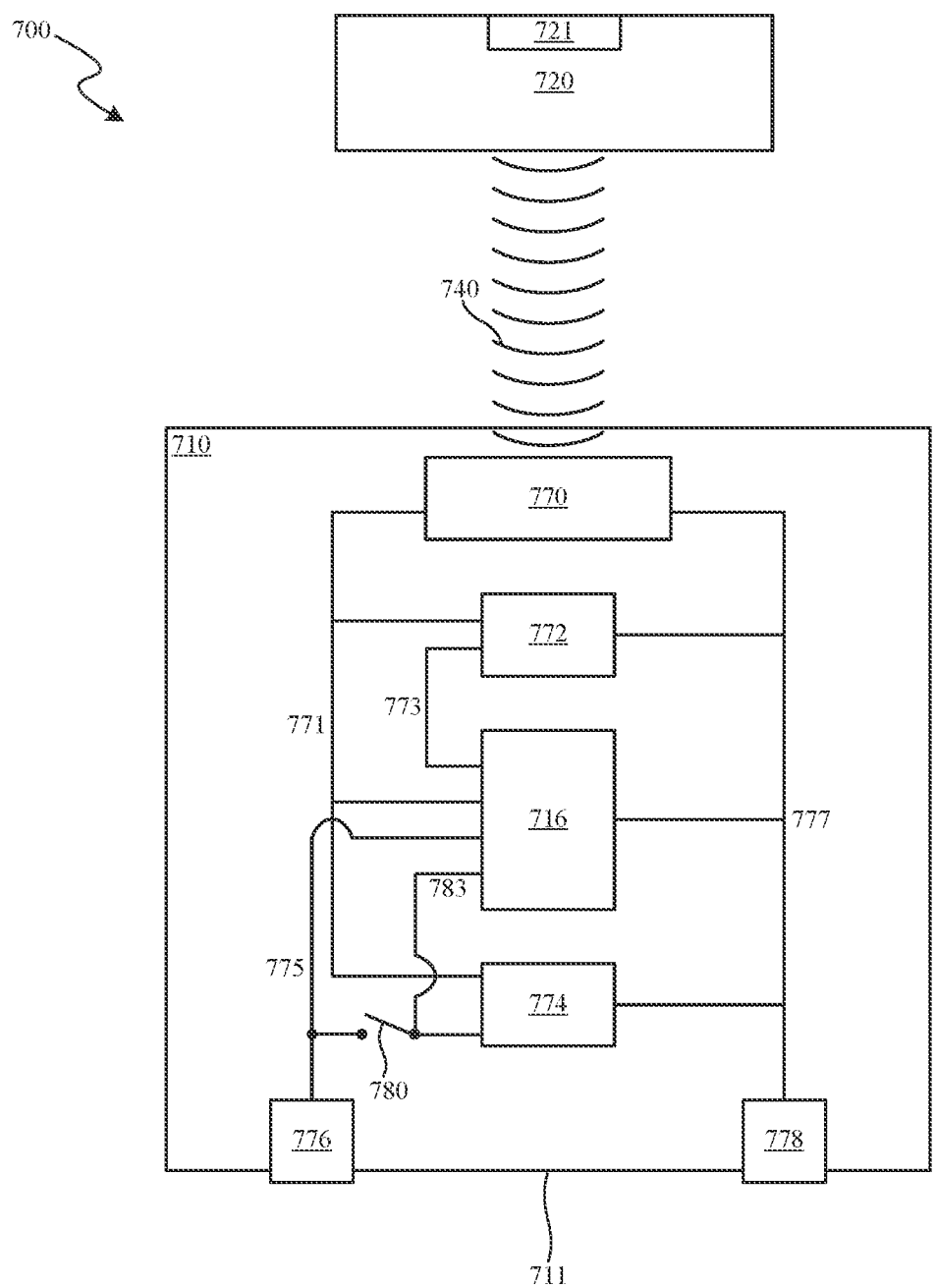
FIG. 7 is a partially schematic diagram of a tissue stimulation system configured in accordance with additional embodiments of the present technology.

FIG. 7 is a partially schematic diagram of a tissue stimulation system 700 ("system 700") configured in accordance with embodiments of the present technology. The system 700 can include several features generally similar or identical to the features of the systems 100, 200, 400, and/or 500 described in detail above with reference to FIGS. 1-5. For example, the system 700 can include a receiver-stimulator 710 in operable communication with a controller-transmitter 720. The controller-transmitter 720 can generate and transmit a signal 740 (e.g., an acoustic ultrasound signal) to the receiver-stimulator 710 including electrical stimulation parameters (e.g., pacing parameters provided by an external programmer, such as the programmer 130 of FIG. 1).

In some embodiments, the controller-transmitter 720 can modulate the signal 740 to include the electrical stimulation parameters. For example, the controller-transmitter 720 can pulse modulate the signal 740 such that a duration of transmission bursts or a time between subsequent transmission bursts encodes the electrical stimulation parameters. In some embodiments, the electrical stimulation parameters can include a minimum pacing rate, a threshold detection level for sensing cardiac depolarization, a pacing pulse output voltage, and/or the like. The receiver-stimulator 710 can receive the signal 740 and convert the signal 740 into electrical power for stimulating tissue according to the electrical stimulation parameters. In some embodiments, the controller-transmitter 720 includes a sensor 721 (e.g., one or more electrodes) for detecting an electrical output of the receiver-stimulator 710.

More specifically, in the illustrated embodiment the receiver-stimulator 710 includes a housing 711 containing and/or carrying a plurality of electronic components including a controller 716, a transducer circuit 770, a first storage unit 772, a second storage unit 774, a cathode 776, and an anode 778 (the cathode 776 and the anode 778 can collectively be referred to as "electrodes"). The cathode 776 and the anode 778 can project past and/or be incorporated into an outer surface of the housing 711 and are configured to be electrically coupled to tissue (e.g., cardiac tissue) of a patient for delivering electrical stimulation energy and/or sensing electrical signals through the tissue. The transducer circuit 770 (e.g., an energy-harvesting circuit) can receive the signal 740, convert the signal 740 to electrical power, and pass the electrical power to the first storage unit 772 and the second storage unit 774 via a first electrical line 771 (e.g., a negative output of the transducer circuit 770). That is, the transducer circuit 770 can harvest the energy from the signal 740 to charge the first and second storage units 772, 774. The first and second storage units 772, 774 can be capacitors, super-capacitors, rechargeable batteries, and/or other components that can store electrical energy. In the illustrated embodiment, the first storage unit 772 powers the controller 716 via a second electrical line 773.

The controller 716 can receive inputs from (i) the transducer circuit 770 via the first electrical line 771, (ii) the cathode 776 via a third electrical line 775 (e.g., a cathode bus), and (iii) the anode 778 via a fourth electrical line 777. A fourth electrical line 777 from the anode 778 can provide a ground reference for the controller 716 and/or other components of the receiver-stimulator 710. In the illustrated embodiment, the second storage unit 774 is electrically coupled to the cathode 776 via a switch 780 (e.g., and the third electrical line 775 and/or one or more additional electrical lines), and provides electrical power to the cathode 776 when the switch 780 is closed. In other embodiments, the switch 780 can be positioned between the second storage unit 774 and the anode 778, and the cathode 776 can be electrically coupled to the first electrical line 771.

In some embodiments, the controller 716 can amplify input signals from the cathode 776 and the anode 778 and apply a detection algorithm to detect certain cardiac events. For example, the controller 716 can apply a threshold-level detector or other suitable algorithm for sensing cardiac depolarization events. The controller 716 can further determine when to electrically stimulate the tissue (e.g., pace the tissue) via the cathode 776 and the anode 778 based on (i) the timing of a sensed cardiac depolarization event (and/or another cardiac event) and/or (ii) the electrical stimulation parameters encoded in the signal 740. To apply the electrical stimulation energy, the controller 716 can output a control signal over a sixth electrical line 783 to (i) close the switch 780 such that the second storage unit 774 delivers the electrical stimulation energy to the cathode 776 and then (ii) open the switch 780 to achieve a desire pacing pulse width.

In some embodiments, the receiver-stimulator 710 can send a communication signal to the controller-transmitter 720 to indicate that the first storage unit 772 and/or the second storage unit 774 are fully charged. For example, the receiver-stimulator 710 can deliver an electrical energy pulse (e.g., a short duration, sub-stimulation pulse) to the cathode 776 that can be detected by the controller-transmitter 720 (e.g., the sensor 721 of the controller-transmitter 710). In other embodiments, the receiver-stimulator 710 can send a radiofrequency or ultrasound signal to the controller-transmitter 720 as described in detail above, for example, with reference to FIGS. 2-4. After receiving the communication signal, the controller-transmitter 720 can terminate the transmission of the signal 740 for a predetermined amount of time.

Figure 8:
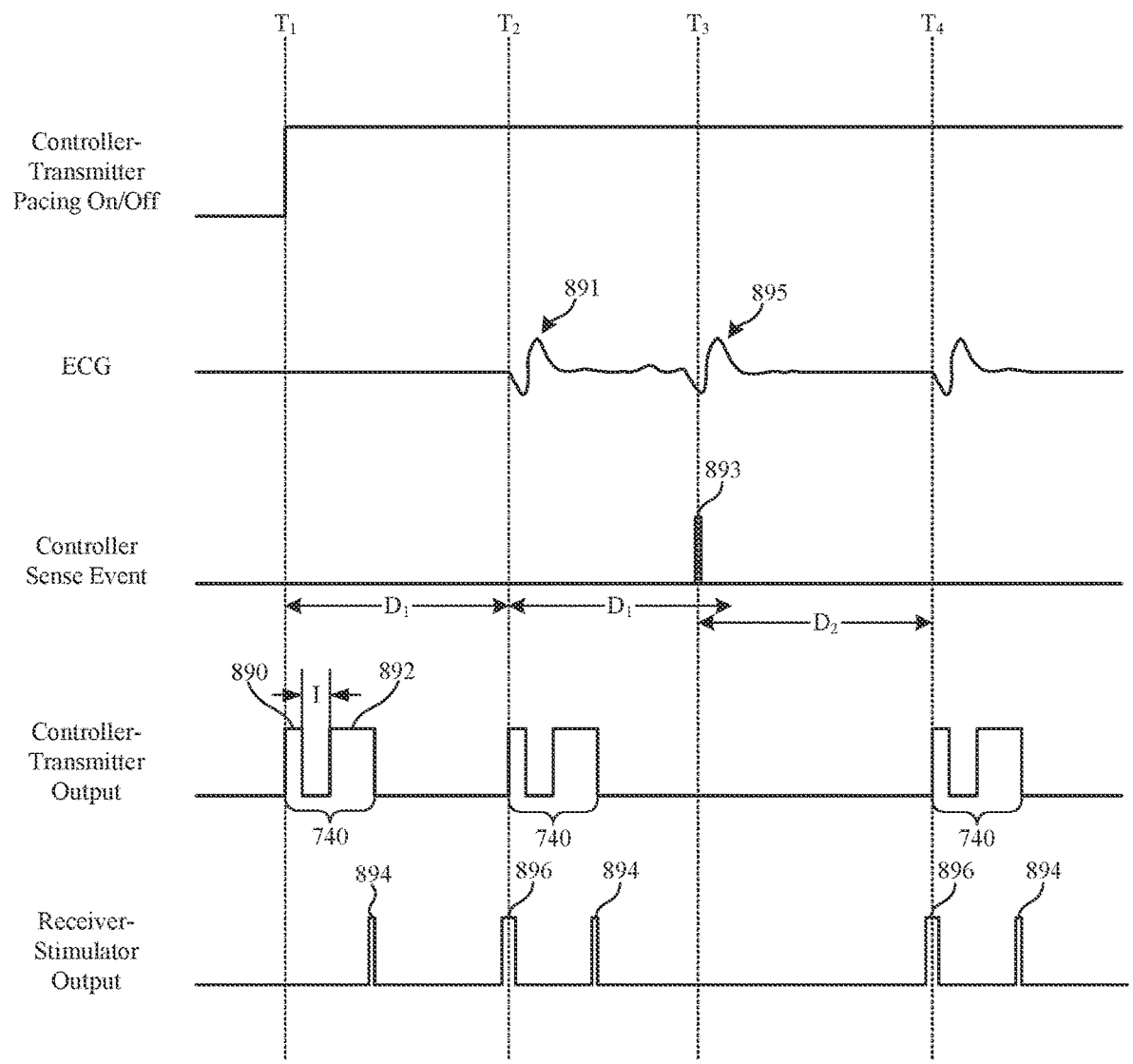
FIG. 8 illustrates an example control scheme and timing sequence for the system of FIG. 7 in a pacemaker application in accordance with embodiments of the present technology.

FIG. 8 illustrates an example control scheme and timing sequence for the system 700 of FIG. 7 in a pacemaker application (e.g., a bradycardia pacemaker application) with the receiver-stimulator 710 (FIG. 7) implanted at a heart of a patient in accordance with embodiments of the present technology. FIG. 8 depicts the evolution over time of (i) the on/off state of the system 700 ("Controller-Transmitter Pacing On/Off"), (ii) the ECG of a patient ("ECG") which is representative of an EMG detected via the cathode 776 and/or the anode 778, (iii) the sensing of a cardiac event by the controller 716 ("Controller Sense Event"), (iv) the acoustic output signal 740 of the controller-transmitter 720 ("Controller-Transmitter Output"), and (v) the electrical output of the receiver-stimulator 710 ("Receiver-Stimulator Output").

In the illustrated embodiment, the system 700 is enabled for a pacing mode at a first time $T_1$ ("turned on"). When the pacing mode is enabled, the controller-transmitter 720 can output the signal 740 including a short first transmission burst 890 and a longer second transmission burst 892 separated by a time interval I. In some embodiments, the time interval I encodes a maximum allowable cardiac interval $D_1$ between heart beats for the pacemaker application. The transducer circuit 770 of the receiver-stimulator 710 can receive the second transmission burst 892 and convert the acoustic energy to electrical energy for charging the first and second storage units 772, 774. In some embodiments, the receiver-stimulator 710 can determine the length of the second transmission burst 892 by, for example, determining when the first and second storage units 772, 774 are sufficiently (e.g., fully) charged and outputting an output signal 894 (e.g., a communication signal, a communication pulse) via the cathode 776 and/or anode 778 indicating that charging is sufficient. The controller-transmitter 720 can detect the output signal 894 (e.g., via the sensor 721) and cease transmission of the signal 740 upon detection. In some embodiments, the output signal 894 is a short-duration electrical signal that is not configured (e.g., has a low enough amplitude and/or duration) to stimulate the heart of the patient. In some aspects of the present technology, this arrangement can ensure that the receiver-stimulator 710 is optimally charged (e.g., to provide a specified output pacing voltage) regardless of the acoustic transfer path between the controller-transmitter 720 and the receiver-stimulator 710 and any changes in the acoustic transfer path over time (e.g., regardless of any variability of the acoustic transfer path over different heart beats).

After receiving the signal 740, the controller 716 can set a timer for the specified cardiac interval $D_1$ while monitoring the heart of the patient to sense a specified cardiac event, such as a cardiac depolarization event in EMG data sensed via the cathode 776 and/or the anode 778. If the controller 716 does not sense the specified cardiac event after the interval $D_1$, the controller 716 can send the control signal to close the switch 780 to deliver all or a portion of the electrical energy stored in the second storage unit 774 to the cathode 776 and/or the anode 778 to stimulate (e.g., pace) the heart of the patient. After a time period equivalent to the desired pacing pulse width, the controller 716 can then send a signal to open the switch 780. In the illustrated embodiment, for example, the receiver-stimulator 710 delivers a pacing pulse 896 at a second time $T_2$ after the cardiac interval $D_1$ has elapsed after the first time $T_1$. The pacing pulse 896 can stimulate the heart to beat, as represented in the sensed ECG by an induced wave 891 following the time $T_2$. After the receiver-stimulator 710 delivers the pacing pulse 896, the controller-transmitter 720 can detect the delivered pacing pulse 896 and recharge the receiver-stimulator 710 by again transmitting the signal 740 to charge the first and second storage units 772, 774, and the receiver-stimulator 710 can cease the transmission of the signal 740 by again outputting the output signal 894 when the first and second storage units 772, 774 are sufficiently charged, If the controller 716 does sense the specified cardiac event during the interval $D_1$, the controller 716 can maintain the switch 780 in the open position such that no stimulation is applied to the heart. For example, in the illustrated embodiment the controller 716 senses the specified cardiac event (e.g., as represented by an event marker 893 corresponding to an intrinsic cardiac activity 895) at a third time $T_3$ during the interval $D_1$ after the second time $T_2$. Accordingly, the receiver-stimulator 710 does not output the pacing pulse 896 and the controller-transmitter 720 does not retransmit the signal 740. At this time, the controller 716 can update the initial interval $D_1$ to a second interval $D_2$ based on the detected event marker 893. The interval $D_1$ can be the same or different than the interval $D_2$.

The continued monitoring of cardiac events, charging of the receiver-stimulator 710, and delivery of the pacing pulse 896 can continue for as long as the pacing mode of the controller-transmitter 710 is enabled. For example, in the illustrated embodiment the receiver-stimulator 710 delivers another pacing pulse 896 at a fourth time $T_4$ after the cardiac interval $D_2$ has elapsed after the third time $T_3$. In some embodiments, the cardiac interval and/or parameters of the pacing pulse 896 can be modified by the controller-transmitter 720 in different transmissions of the signal 740 (e.g., by changing the initial interval $D_1$ to a second interval $D_2$). Moreover, additional information and/or parameters can be encoded in the signal 740 by, for example, breaking the signal 740 up into additional bursts. In such embodiments, a delay between each burst can correspond to a different parameter.

The following examples are illustrative of several embodiments of the present technology:

1. A system for pacing cardiac tissue of a patient, comprising:
  a controller-transmitter including a first circuit and a second circuit, wherein the first circuit is configured to transmit an acoustic signal, and wherein the second circuit is configured to receive a radiofrequency signal; and
  a receiver-stimulator configured to be implanted in the patient proximate the cardiac tissue, wherein the receiver-stimulator includes—
    an electrode;
    a third circuit operably coupled to the electrode and configured to receive at least a portion of the acoustic signal and convert the acoustic signal to electrical energy for delivery to the cardiac tissue via the electrode to electrically pace the cardiac tissue; and
    a fourth circuit configured to transmit the radiofrequency signal to the second circuit of the controller-transmitter.
2. The system of example 1 wherein the receiver-stimulator further comprises a physiological sensor configured to sense a physiological parameter of the patient, and wherein the radiofrequency signal includes information about the sensed physiological parameter.
3. The system of example 2 wherein the sensed physiological parameter is an intracardiac electrogram (IEGM).
4. The system of example 2 wherein the sensed physiological parameter is a cardiac sound.
5. The system of any one of examples 2-4 wherein the controller-transmitter further comprises a controller electrically coupled to the first circuit and the second circuit, wherein the controller is configured to control the first circuit to transmit the acoustic signal based at least in part on the sensed physiological parameter.
6. The system of any one of examples 1-5 wherein the radiofrequency signal includes information about a status of the receiver-stimulator.
7. The system of any one of examples 1-6 wherein the radiofrequency signal includes information about an efficiency of delivery of the electrical energy to the cardiac tissue.
8. The system of any one of examples 1-7 wherein—
the radiofrequency signal is a first radiofrequency signal;
the controller-transmitter further comprises a fifth circuit configured to transmit a second radiofrequency signal to the receiver-stimulator; and
the receiver-stimulator further comprises an energy-harvesting circuit configured to receive the second radiofrequency signal and convert the second radiofrequency signal to electrical energy.
9. The system of example 8 wherein the receiver-stimulator further comprises a controller configured to control a timing of the delivery of the electrical energy from the third circuit to the cardiac tissue, and wherein the controller is configured to be at least partially powered by the electrical energy from the energy-harvesting circuit.
10. The system of example 8 or example 9 wherein the receiver-stimulator further comprises a physiological sensor configured to sense a physiological parameter of the patient, and wherein the physiological sensor is configured to be at least partially powered by the electrical energy from the energy-harvesting circuit.
11. The system of example 10 wherein the receiver-stimulator further comprises a controller configured to (a) receive the electrical energy from the energy-harvesting circuit and the physiological parameter from the physiological sensor and (b) control the fourth circuit to produce the first radiofrequency signal including encoded information about the physiological parameter.
12. A method of delivering electrical stimulation energy to a heart of a patient, the method comprising:
receiving, at a controller-transmitter implanted within the patient, a cardiac signal indicative of a function of the heart;
determining, via the controller-transmitter, a temporal spacing between a selected number of beats of the heart based on the received cardiac signal;
determining, via the controller-transmitter, an average temporal spacing between the beats to determine a pacing pulse interval;

wirelessly transmitting a signal from the controller-transmitter to a receiver-stimulator implanted in cardiac tissue, wherein the signal is associated with the pacing pulse interval; and delivering, via the receiver-stimulator, the electrical stimulation energy to the heart according to the pacing pulse interval.

13. The method of example 12 wherein the cardiac signal includes a waveform, and wherein determining the temporal spacing does not include determining an amplitude or morphology of the waveform.

14. The method of example 12 or example 13 wherein the cardiac signal is an electrocardiogram (ECG) signal.

15. The method of example 12 or example 13 wherein the cardiac signal is a plethysmography signal.

16. The method of example 12 or example 13 wherein the cardiac signal is an audio signal.

17. The method of any one of examples 12-16 wherein the pacing pulse interval is a first pacing pulse interval, and wherein the method further comprises:

receiving a pacing signal from a co-implant device implanted in the patient;

determining a second pacing pulse interval based on the pacing signal;

averaging the first and second pacing pulse intervals to determine a third pacing pulse interval; and delivering the electrical stimulation to the heart according to the third pacing pulse interval.

18. The method of example 17 wherein the co-implant device is an implantable cardioverter defibrillator (ICD) or a pacemaker.

19. The method of any one of examples 12-18 wherein receiving the cardiac signal includes receiving the cardiac signal at the controller-transmitter from the receiver-stimulator implanted at the heart of the patient, wherein the controller-transmitter is configured to transmit acoustic energy to the receiver-stimulator, and wherein the receiver-stimulator is configured to convert the acoustic energy to the electrical stimulation energy and deliver the electrical stimulation energy to the heart.

20. A system for stimulating tissue of a patient, comprising:

a controller-transmitter configured to transmit an acoustic signal; and a receiver-stimulator configured to be implanted in the patient proximate the tissue, wherein the receiver-stimulator includes— an electrode;

a transducer circuit configured to receive at least a portion of the acoustic signal and convert the acoustic signal to electrical energy;

a storage unit electrically coupled to the transducer circuit and configured to store at least a portion of the electrical energy;

a switch configured to selectively electrically couple the storage unit to the electrode; and a controller electrically coupled to the switch, wherein the controller is configured to control the switch to deliver the electrical energy from the storage unit to the electrode for output to the tissue as a first electrical pulse and a second electrical pulse, wherein the second electrical pulse is configured to stimulate the tissue, and wherein the controller-transmitter is configured to detect the first electrical pulse and to cease transmission of the acoustic signal in response to detecting the first electrical pulse.

21. The system of example 20 wherein the first electrical pulse does not stimulate the tissue.

22. The system of example 20 or example 21 wherein the first electrical pulse has a shorter pulse width than the second electrical pulse.

23. The system of any one of examples 20-22 wherein the tissue is cardiac tissue, wherein the controller-transmitter is configured to encode a cardiac interval for the cardiac tissue in the acoustic signal, and wherein the controller of the receiver-stimulator is further configured to— sense a depolarization of the cardiac tissue;

detect the cardiac interval in the acoustic signal;

initiate a timer for the cardiac interval; and if the depolarization is not sensed during the cardiac interval, control the switch to deliver the second stimulation pulse after the timer has elapsed.

24. The system of any one of examples 20-23 wherein the controller is configured to control the switch to deliver the first stimulation pulse based on a charge state of the storage unit.

25. The system of any one of examples 20-24 wherein the controller-transmitter is configured to detect the second electrical pulse and to again transmit the acoustic signal to the receiver-stimulator in response to detecting the second electrical pulse.

The above detailed description of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments can perform steps in a different order. Likewise, the various electronic components and functions can be separated into more or fewer electronic circuit elements and/or functional blocks. The various components and/or functionalities of the embodiments described herein can also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms can also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications can be made without deviating from the technology. Further, while advantages associated with some embodiments of the technology have been described in the context of those embodiments, other embodiments can also exhibit such advantages, and not all embodiments need necessarily exhibit such advantages to fall within the scope of the technology. Accordingly, the disclosure and associated technology can encompass other embodiments not expressly shown or described herein.

We claim:

1. A system for pacing cardiac tissue of a patient, comprising:
   a controller-transmitter including a first circuit and a second circuit, wherein the first circuit is configured to transmit an acoustic signal, and wherein the second circuit is configured to receive a radiofrequency signal; and
   a receiver-stimulator configured to be implanted in the patient proximate the cardiac tissue, wherein the receiver-stimulator includes—
      an electrode;
      a third circuit operably coupled to the electrode and configured to receive at least a portion of the acoustic signal and convert the acoustic signal to electrical energy for delivery to the cardiac tissue via the electrode to electrically pace the cardiac tissue; and
      a fourth circuit configured to transmit the radiofrequency signal to the second circuit of the controller-transmitter;
   wherein the control-transmitter is configured to modify the acoustic signal based on the radiofrequency signal to control the electrical energy delivered to the cardiac tissue via the electrode to control the electrical pacing of the cardiac tissue.

2. The system of claim 1 wherein the receiver-stimulator further comprises a physiological sensor configured to sense a physiological parameter of the patient, and wherein the radiofrequency signal includes information about the sensed physiological parameter.

3. The system of claim 2 wherein the sensed physiological parameter is an intracardiac electrogram (IEGM).

4. The system of claim 2 wherein the sensed physiological parameter is a cardiac sound.

5. The system of claim 2 wherein the controller-transmitter further comprises a controller electrically coupled to the first circuit and the second circuit, wherein the controller is configured to control the first circuit to transmit the acoustic signal based at least in part on the sensed physiological parameter.

6. The system of claim 1 wherein the radiofrequency signal includes information about a status of the receiver-stimulator.

7. The system of claim 1 wherein the radiofrequency signal includes information about an efficiency of delivery of the electrical energy to the cardiac tissue.

8. The system of claim 1 wherein—
   the radiofrequency signal is a first radiofrequency signal;
   the controller-transmitter further comprises a fifth circuit configured to transmit a second radiofrequency signal to the receiver-stimulator; and
   the receiver-stimulator further comprises an energy-harvesting circuit configured to receive the second radiofrequency signal and convert the second radiofrequency signal to electrical energy.

9. The system of claim 8 wherein the receiver-stimulator further comprises a controller configured to control a timing of the delivery of the electrical energy from the third circuit to the cardiac tissue, and wherein the controller is configured to be at least partially powered by the electrical energy from the energy-harvesting circuit.

10. The system of claim 8 wherein the receiver-stimulator further comprises a physiological sensor configured to sense a physiological parameter of the patient, and wherein the physiological sensor is configured to be at least partially powered by the electrical energy from the energy-harvesting circuit.

11. The system of claim 10 wherein the receiver-stimulator further comprises a controller configured to (a) receive the electrical energy from the energy-harvesting circuit and the physiological parameter from the physiological sensor and (b) control the fourth circuit to produce the first radiofrequency signal including encoded information about the physiological parameter.

* * * * *